US011597977B2

(12) United States Patent
Lo et al.

(10) Patent No.: US 11,597,977 B2
(45) Date of Patent: *Mar. 7, 2023

(54) MARKER FOR PRENATAL DIAGNOSIS AND MONITORING

(71) Applicant: The Chinese University of Hong Kong, Hong Kong (CN)

(72) Inventors: Yuk Ming Dennis Lo, Hong Kong (CN); Wai Kwun Rossa Chiu, Hong Kong (CN); Stephen Siu Chung Chim, Hong Kong (CN); Yu-Kwan Tong, Hong Kong (CN); Chunming Ding, Hangzhou (CN)

(73) Assignee: The Chinese University of Hong Kong, Hong Kong (CN)

( * ) Notice: Subject to any disclaimer, the term of this patent is extended or adjusted under 35 U.S.C. 154(b) by 405 days.

This patent is subject to a terminal disclaimer.

(21) Appl. No.: 16/806,820

(22) Filed: Mar. 2, 2020

(65) Prior Publication Data

US 2020/0270694 A1 Aug. 27, 2020

Related U.S. Application Data

(60) Division of application No. 15/842,718, filed on Dec. 14, 2017, now Pat. No. 10,604,808, which is a continuation of application No. 15/012,611, filed on Feb. 1, 2016, now Pat. No. 9,862,999, which is a continuation of application No. 13/215,024, filed on Aug. 22, 2011, now abandoned, which is a division of application No. 12/724,335, filed on Mar. 15, 2010, now Pat. No. 8,026,067, which is a division of application No. 11/144,951, filed on Jun. 3, 2005, now Pat. No. 7,709,194.

(60) Provisional application No. 60/577,242, filed on Jun. 4, 2004.

(51) Int. Cl.
C12Q 1/6883 (2018.01)
C12Q 1/6827 (2018.01)

(52) U.S. Cl.
CPC ......... *C12Q 1/6883* (2013.01); *C12Q 1/6827* (2013.01); *C12Q 2600/154* (2013.01); *C12Q 2600/156* (2013.01)

(58) Field of Classification Search
None
See application file for complete search history.

(56) References Cited

U.S. PATENT DOCUMENTS

| 6,258,540 | B1 | 7/2001 | Lo et al. | |
|---|---|---|---|---|
| 6,927,028 | B2 | 8/2005 | Lo et al. | |
| 7,655,399 | B2 | 2/2010 | Cantor et al. | |
| 7,709,194 | B2 * | 5/2010 | Lo | C12Q 1/6883 536/23.1 |
| 8,026,067 | B2 * | 9/2011 | Lo | C12Q 1/6827 435/6.1 |
| 9,862,999 | B2 * | 1/2018 | Lo | C12Q 1/6883 |
| 10,604,808 | B2 * | 3/2020 | Lo | C12Q 1/6827 |
| 2003/0211522 | A1 | 11/2003 | Landes et al. | |

OTHER PUBLICATIONS

Amicucci, et al., "Prenatal Diagnosis of Myotonic Dystrophy Using Fetal DNA Obtained from Maternal Plasma," Clinical Chemistry, 2000, vol. 46, No. 2, pp. 301-302.
Bolze et al., (Int. J. Mol. Med. vol. 12, No. 4, pp. 479-484, Oct. 2003).
Chen et al., PLoS One 6(7): e21791 2011.
Chim, et al., "Detection of the placental epigenetic signature of the maspin gene in material plasma," PNAS, Oct. 11, 2005, vol. 102, No. 41, pp. 14753-14758.
Chiu, et al., "Prenatal Exclusion of ß Thalassaemia Major by Examination of Maternal Plasma," The Lancet, Sep. 28, 2002, vol. 360, pp. 998-1000.
Costello, et al., "Methylation matters: a new spin on maspin," Nature Genetics, Jun. 2002, vol. 3, p. 123.
Dokras, et al., "The Tumour Suppressor Gene Maspin is Differentially Regulated in Cytotrophoblasts During Human Placental Development," Elsevier Science Ltd., 2002, vol. 23,. pp. 274-280.
Futscher, Nature Genetics, vol. 31, No. 2, (May 20, 2002) pp. 175-179.
Futscher, et al., "Role for DNA Methylation in the Control of Cell Type-Specific Maspin Expression," Nature Genetics, Jun. 2002, vol. 31, pp. 175-179.
Ionnidis, PLoS Med, 2001, 2(8):e124; pp. No. 696-0701.
Ko et al., Ultrasound Obstet Gynecol. Mar. 2009; 33(3):259-64.
Leung, Tse N., "Increased Maternal Plasma Fetal DNA Concentrations in Women Who Eventually Develop Preclampsia," Clinical Chemistry, 2001, vol. 41, No. 1, pp. 137-139.
Lo, et al., "Increased Fetal DNA Concentrations in the Plasma of Pregnant Women Carrying Fetuses with Trisomy 21," Clinical Chemistry, 1999, vol. 45, No. 10, pp. 1747-1751.
Lo, et al., "Presence of Fetal DNA in Maternal Plasma and Serum," The Lance, Aug. 16, 1997. vol. 350, pp. 485-487.
Lo, et al. "Plasma placental RNA allelic ratio permits noninvasive prenatal chromosomal aneuploidy detection." Nature medicine 13, No. 2 (2007): 218-223.
Lo, et al., "Quantitative Abnormalities of Fetal DNA in Maternal Serum in Preeclampsia," Clinical Chemistry, 1999, vol. 45, No. 2, pp. 184-188.
Maass, et al., "Hypermethylation and histone deacetylation lead to silencing of the maspin gene in human breast cancer," BBRC, 2002,. vol. 297, pp. 125-128.
Misumi et al., Advances in Medicine and Biology, vol. 5, Chapter 5, 2011).

(Continued)

*Primary Examiner* — Jeanine A Goldberg
(74) *Attorney, Agent, or Firm* — Kilpatrick Townsend & Stockton LLP

(57) ABSTRACT

The present invention relates to new methods for diagnosing a pregnancy-associated disorder by analyzing fetal DNA present in the mother's blood. More specifically, this invention relies on the discovery that the maspin gene is differentially methylated in fetal DNA and in maternal DNA and provides these new diagnostic methods, which distinguish fetal DNA from maternal DNA and detect prenatal disorders based on abnormalities in fetal DNA level and methylation status.

16 Claims, 15 Drawing Sheets

Specification includes a Sequence Listing.

(56) References Cited

OTHER PUBLICATIONS

Pennisi, "A Closer Look at SNPs Suggests Difficulties," Science, New Series, vol. 281, No. 5384, Sep. 1998, pp. 1787-1789.
Poon, et al.; "Differential DNA Methylation between Fetus and Mother as a Strategy for Detecting Fetal DNA in Maternal Plasma," 2002, Clinical Chemistry, vol. 48, No. 1, pp. 35-41.
Saito, et al., "Prenatal DNA Diagnosis of a Single-Gene Disorder from Maternal Plasma,"The Lancet, Sep. 30, 2000, vol. 356, p. 1170.
Sekizawa, et al.; "Cell-free Fetal DNA is Increased in Plasma of Women with Hyperemesis Gravidarum"; 2001, Clinical Chemistry, vol. 47, No. 12, pp. 2164-2165.
Thisted, "What is a P-Value?" May 25, 1998.
Tong, et al., "Noninvasive Prenatal Detection of Fetal Trisomy 18 by Epigenetic Allelic Ratio Analysis in Maternal Plasma: Theoretical and Empirical Considerations," 2006, Clinical Chemistry, vol. 52, No. 12, pp. 2194-2202.
Zhang, et al. "Transactivation through Ets and Ap1 transcription sites determines the expression of the tumor-suppressing gene maspin." Cell growth & differentiation: the molecular biology journal of the American Association for Cancer Research 8, No. 2 (1997): 179-186.
Zhong, et al., "Elevation of Both Maternal and Fetal Extracellular Circulating Deoxyribonucleic Acid Concentrations in the Plasma of Pregnant Women with Preeclampsia," Am J. Obstet Gynecol, Feb. 2001, pp. 414-419.
Zhong, et at., "High Levels of Fetal Erythroblasts and Fetal Extracellular DNA in the Peripheral Blood of a Pregnant Women with Idiopathic Polyhydramnios: Case Report," Prenatal Diagnosis, 2000, vol. 20, pp. 838-841.
Zou, et al., "Maspin, a Serpin with Tumor-Suppressing Activity in Human Mammary Epithelial Cells," Science, Jan. 28, 1994, vol. 263, pp. 526-529.
European Examination Report dated Apr. 19, 2010, issued in related European Patent Application No. EP 05746652.6, filed Jun. 6, 2005.
Zhong et al., "Fetal DNA in maternal plasma is elevated in pregnancies with aneuploid fetuses," 2000, Prenatal Diagnosis, 20, pp. 795-798.

* cited by examiner

```
TGGGTAGTTATTTTTTTTGGTATTTAGTAGAATGAGTTGTTGTAGTTTATATAAAAGAA
                                                         >>>

TGGAGATTAGAGTATTTTTTGTGTTATTAACGTGTTTGAGAAATTTGTAGTGTTATTATT
>>>>>>>>>-F->>>>>>>>>>>>>>>    -247

ATTATATATTATTTTTATTTTATCGAATATTTTATTTTTCGGTTTTGCGTGGGTCGAGAG
                -194              -178      -170    -163
          TTATCGAATATTTTATTTTTCGGTTTcGC              MF
        TTTTATTTTATTGAATATTTTATTTTTTGGTTTcGT          UF
                                       TGGGTYGAGAG   MP
                                       TGGGTTGAGAG   UP

GATTGTCGTACGTATGTTTGTACGTATGTATGTAATTTATAGTTTTTTTTGTTCGAATA
 -151  -147        -135                          -103<<<
         GCgTACAAACATGCATACATACATTAAATATCAAAAAA      MR
         ACgTACAAACATACATACATACATTAAATATCAAAAAAA     UR
GATTGT                                              MP
GATTGT                                              UP

TGTTGGAGGTTTTTTGGAAGTTGTGTAGATAATAGTAATTTTAGTTTGAATTATTTTTTT
<<<<<<<-R-<<<<<<<<<<<
```

*FIG. 2* maternal plasma
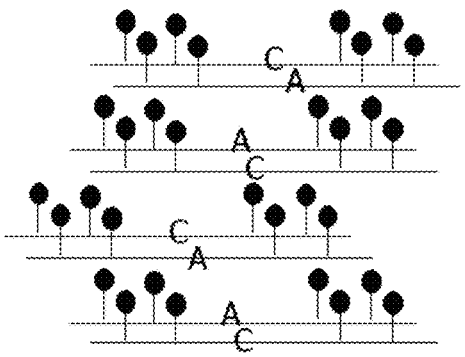
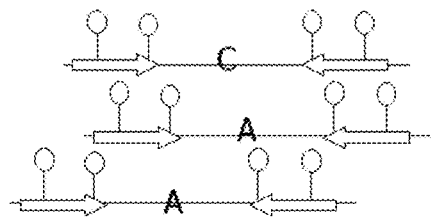
No U-*maspin* PCR product
U-*maspin* PCR product 
Allelic ratio determination
*FIG. 5*

Fig. 6A. 1st trimester, chorionic villus sample
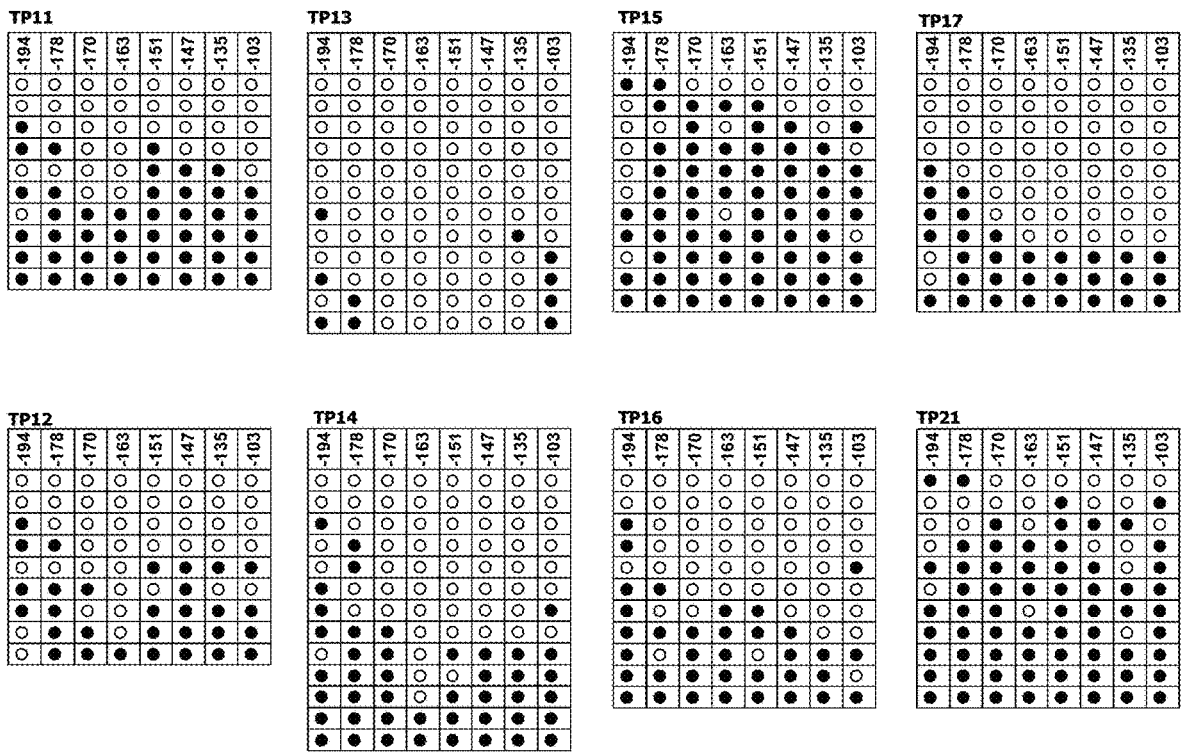
Fig. 6B. 1st trimester, maternal buffy coat
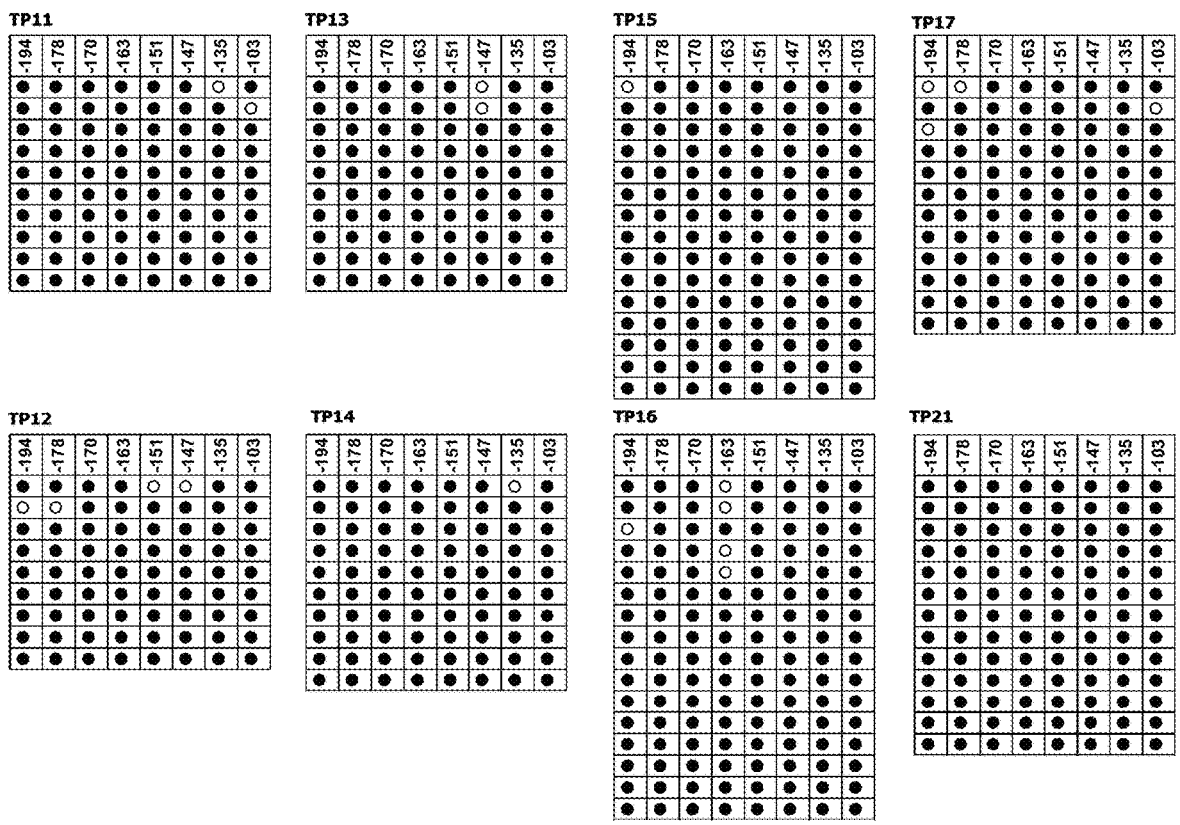

Fig. 6C. 3rd trimester, placenta
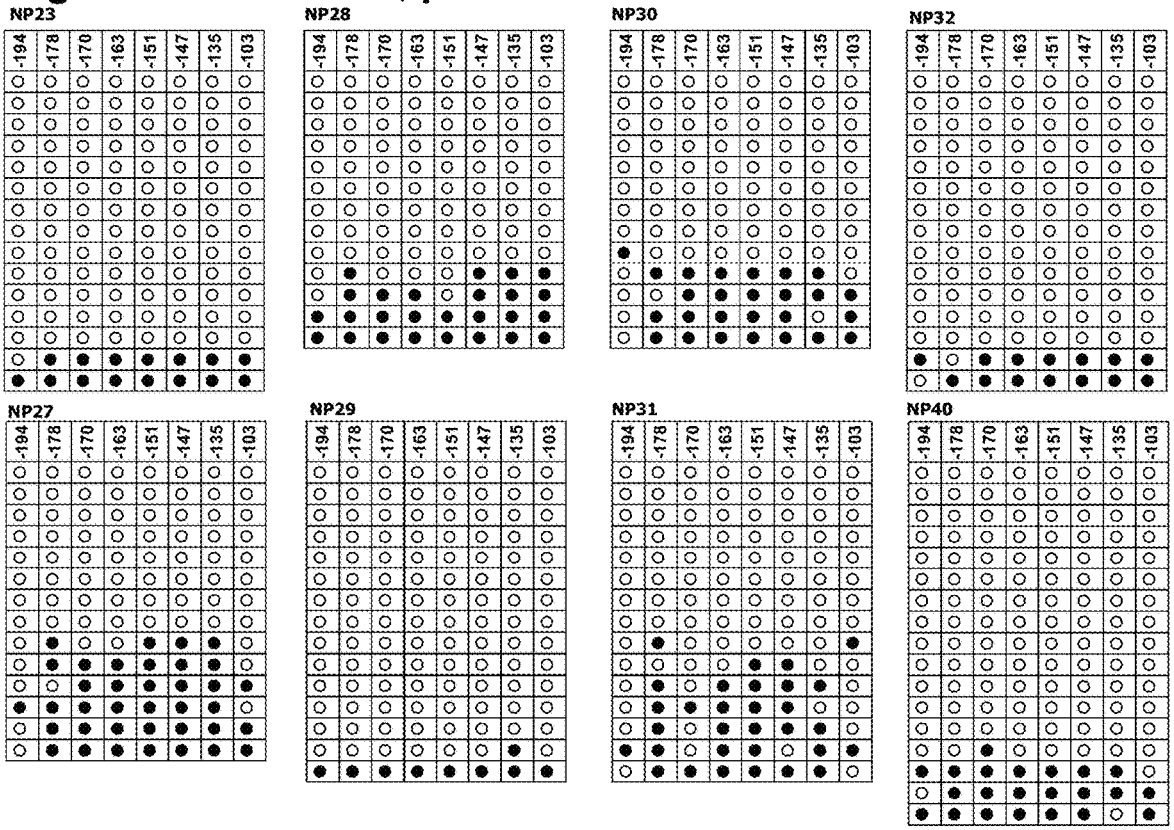
Fig. 6D. 3rd trimester, maternal buffy coat
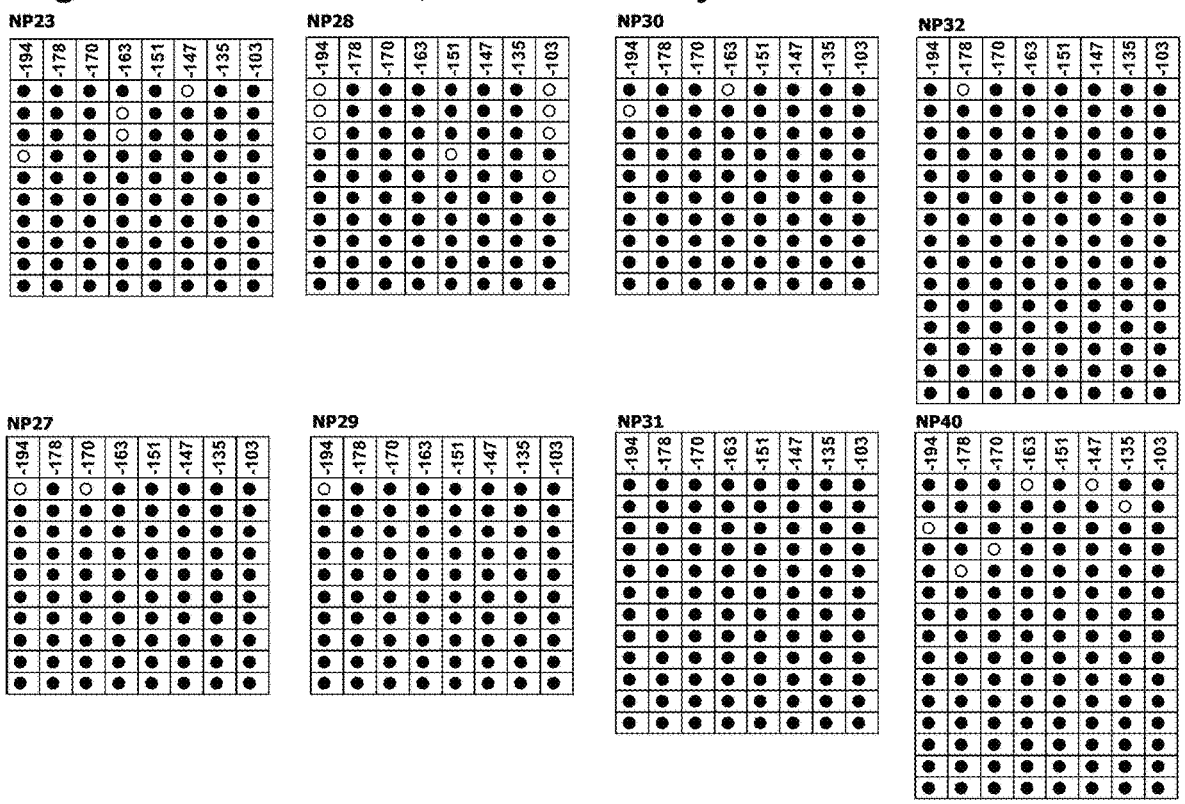

MARKER FOR PRENATAL DIAGNOSIS AND MONITORING

This application is a continuation of U.S. patent application Ser. No. 15/842,718, filed Dec. 14, 2017, now U.S. Pat. No. 10,604,808, which is a continuation of U.S. patent application Ser. No. 15/012,611, filed Feb. 1, 2016, now U.S. Pat. No. 9,862,999, which is a continuation of U.S. patent application Ser. No. 13/215,024, filed Aug. 22, 2011 now abandoned, which is a division of U.S. patent application Ser. No. 12/724,335, filed Mar. 15, 2010, now U.S. Pat. No. 8,026,067, which is a division of U.S. patent application Ser. No. 11/144,951, filed Jun. 3, 2005, now U.S. Pat. No. 7,709,194, which claims priority to U.S. provisional patent application No. 60/577,242, filed Jun. 4, 2004, the contents of each of the above are herein incorporated by reference in the entirety.

BACKGROUND OF THE INVENTION

Early detection of pregnancy-related conditions, including potential complications during pregnancy or delivery and genetic defects of the fetus is of crucial importance, as it allows early medical intervention necessary for the safety of both the mother and the fetus. Prenatal diagnosis has been routinely conducted using cells isolated from the fetus through procedures such as chorionic villus sampling (CVS) or amniocentesis. These conventional methods are, however, invasive and present an appreciable risk to both the mother and the fetus despite most careful handling (Tabor et al., *Lancet* 1:1287-1293, 1986).

Alternatives to these invasive approaches have been developed for prenatal screening, e.g., to detecting fetal abnormalities, following the discoveries that several types of fetal cells can be found in maternal circulation (Johansen et al., *Prenat. Diagn.* 15:921-931, 1995) and more importantly, circulating cell-free fetal DNA can be detected in maternal plasma and serum (Lo et al., *Lancet* 350:485-487, 1997). The amount of fetal DNA in maternal blood has been shown to be sufficient for genetic analysis without complex treatment of the plasma or serum, in contrast to the necessary steps for isolating and enriching fetal cells. Fetal rhesus D (RhD) genotyping (Lo et al., *N. Engl. J. Med.* 339:1734-1738, 1998), fetal sex determination (Costa et al., *N. Engl. J. Med.* 346:1502, 2002), and diagnosis of several fetal disorders (Amicucci et al., *Clin. Chem.* 46:301-302, 2000; Saito et al., *Lancet* 356:1170, 2000; and Chiu et al., *Lancet* 360:998-1000, 2002) have since been achieved by detecting fetal DNA in maternal blood using a polymerase chain reaction (PCR)-based technique.

In addition, quantitative abnormalities of fetal DNA in maternal plasma/serum have been reported in preeclampsia (Lo et al., *Clin. Chem.* 45:184-188, 1999 and Zhong et al., *Am. J. Obstet. Gynecol.* 184:414-419, 2001), fetal trisomy 21 (Lo et al., *Clin. Chem.* 45:1747-1751, 1999 and Zhong et al. *Prenat. Diagn.* 20:795-798, 2000) and hyperemesis gravidarum (Sekizawa et al., *Clin. Chem.* 47:2164-2165, 2001). Detection of fetal nucleic acid in maternal blood for prenatal genetic analysis is also disclosed in U.S. Pat. No. 6,258,540.

Fetal RNA present in maternal blood has also been established as a diagnostic tool for pregnancy-associated conditions. For instance, U.S. patent application Ser. No. 09/876,005 discloses non-invasive techniques based on detection of fetal RNA in maternal blood; U.S. patent application Ser. No. 10/759,783 further discloses that the amount of certain mRNA species (e.g., hCG-β, hCRH, hPL, KISS1, TPFI2, and PLAC1) present in maternal blood can be used as markers for diagnosing, monitoring, or predicting pregnancy-related disorders such as preeclampsia, fetal chromosomal aneuploidy, and preterm labor.

Although the stability of DNA provides an advantage for fetal DNA-based diagnosis, one major limitation does exist for this approach: both fetal and maternal DNA is present in the acellular portion of a pregnant woman's blood, e.g., serum or plasma. Thus, there is a need to distinguish fetal DNA from maternal DNA to ensure accurate diagnosis. It was first disclosed in U.S. patent application Ser. No. 09/944,951, published as 20030044388, that fetal and maternal DNA may be distinguished by their different methylation profile. Landes et al. in U.S. Patent Application Publication No. 20030211522 also proposed differential methylation markers may be used for prenatal diagnosis. In the present disclosure, one particular gene, the mammary serine protease inhibitor (maspin) gene, is identified for the first time as a gene containing regions differentially methylated in genomic DNA originated from a fetus or from an adult (e.g., a pregnant women) due to the different status of gene expression. Thus, the differentially methylated fetal maspin gene allows proper identification or quantification of fetal and maternal DNA and therefore reliable diagnosis of prenatal conditions.

BRIEF SUMMARY OF THE INVENTION

In one aspect, this invention relates to a method for detecting or monitoring a pregnancy-associated disorder in a woman pregnant with a fetus. This method comprises the following steps: (a) obtaining a blood sample from the woman; (b) determining the methylation status of at least a portion of the maspin gene in the blood sample, wherein the portion of the maspin gene from the fetus and the portion from the woman are differentially methylated, thereby distinguishing the maspin gene from the woman and the maspin gene from the fetus in the blood sample; (c) determining the level of the fetal maspin gene; and (d) comparing the level of the fetal maspin gene with a standard control. In some cases, an increase from the standard control indicates the presence or progression of a pregnancy-associated disorder. In other cases, a decrease from the standard control indicates the presence or progression of a pregnancy-associated disorder.

In some embodiments, the blood sample is whole blood. In other embodiments, the blood sample is plasma or serum. In an exemplary embodiment, the portion of the maspin gene from the woman is methylated and the portion from the maspin gene from the fetus is less methylated. In another exemplary embodiment, step (b) is performed by treating the DNA present in the blood sample with a reagent that differentially modifies methylated and non-methylated DNA. An often-used reagent for differential modification of methylated and non-methylated DNA is bisulfite. Other suitable regents may include one or more enzymes that preferentially cleave either methylated or unmethylated DNA. Pregnancy-associated disorders can be detected or monitored by this method include preeclampsia, preterm labor, hyperemesis gravidarum, ectopic pregnancy, fetal chromosomal aneuploidy (such as trisomy 18, 21, or 13), and intrauterine growth retardation.

In another aspect, this invention provides a method for detecting or monitoring a pregnancy-associated disorder in a woman pregnant with a fetus. The method comprises the following steps: (a) obtaining DNA in a blood sample from the woman; (b) treating the DNA from step (a) with bisulfite;

(c) performing an amplification reaction using the DNA from step (b) and two primers to amplify at least a portion of the maspin gene, wherein the portion of the maspin gene from the fetal DNA and the portion of the maspin gene from the maternal DNA in the blood sample are differentially methylated, and wherein at least one of the two primers binds differentially to the portion of the maspin gene from the fetus; and (d) comparing the level of the amplified portion of the maspin gene from step (c) with a standard control. In some cases, an increase from the standard control indicates the presence or progression of a pregnancy-associated disorder. In other cases, a decrease from the standard control indicates the presence or progression of a pregnancy-associated disorder.

In some embodiments, the blood sample is whole blood. In other embodiments, the blood sample is plasma or serum. Some exemplary amplification reactions include polymerase chain reaction (PCR), nucleic acid sequence based amplification, strand displacement reaction, and branched DNA amplification reaction. Pregnancy-associated disorders can be detected or monitored by this method include preeclampsia, preterm labor, hyperemesis gravidarum, ectopic pregnancy, fetal chromosomal aneuploidy (such as trisomy 18, 21, or 13), and intrauterine growth retardation.

In a further aspect, this inventions relates to a method for detecting the maspin gene from a fetus in the blood of a pregnant woman. The method comprises the following steps: (a) obtaining a blood sample from the woman; and (b) detecting at least a portion of the maspin gene, wherein the portion of the maspin gene is differentially methylated from the portion of the maspin gene from the maternal DNA in the blood sample, thereby detecting the maspin gene from the fetus. In some embodiments, the blood sample is whole blood. In other embodiments, the blood sample is plasma or serum.

In a yet further aspect, the invention relates to a method for detecting and monitoring a pregnancy-associated disorder. This method comprises the following steps: (a) obtaining DNA in a blood sample from the woman; (b) treating the DNA from step (a) with a reagent that differentially modifies methylated and non-methylated DNA; (c) determining the nucleotide sequence of at least a portion of the maspin gene from step (b); and (d) comparing the profile of the nucleotide sequences from step (c) with a standard control, wherein a change in the profile from the standard control indicates the presence or progression of a pregnancy-associated disorder.

In some embodiments, the reagent comprises bisulfite. Or the reagent may include one or more enzymes that preferentially cleave DNA when the DNA is either methylated or unmethylated. In other embodiments, the blood sample is plasma or serum. In other embodiments, the method further comprises an amplification step of using the DNA from step (b) and two primers to amplify a portion of the maspin gene, wherein the portion of the maspin gene from the fetal DNA and the portion from the maternal DNA in the blood sample are differentially methylated, and wherein at least one of the two primers binds differentially to the portion of the maspin gene from the fetus. In an exemplary embodiment, the amplification step is performed by polymerase chain reaction (PCR) or methylation-specific PCR; in another exemplary embodiment, step (c) is performed by mass spectrometry, primer extension, polynucleotide hybridization, real-time PCR, or electrophoresis.

In an additional aspect, this invention relates to a method for detecting trisomy 18 in a fetus in a pregnant woman. This method comprises the following steps: (a) obtaining DNA from a blood sample from the woman; (b) treating the DNA from step (a) with a reagent that differentially modifies methylated and non-methylated DNA; and (c) determining the levels of different alleles of the maspin gene from the fetal DNA, thereby determining the ratio of the alleles, wherein the different alleles have different methylation profile in at least portion of the maspin gene, and wherein an increase or a decrease in the ratio from a standard control indicates the presence of trisomy 18 in the fetus.

In some embodiments, the reagent comprises bisulfite. Or the reagent may include one or more enzymes that preferentially cleave DNA when the DNA is either methylated or unmethylated. In other embodiments, the blood sample is plasma or serum. In yet other embodiments, placental tissues or other fetal tissues may be used for comparison. In other embodiments, the method further comprises an amplification step of using the DNA from step (b) to amplify of at least a portion of the maspin gene that is differentially methylated in the maspin gene from the fetal DNA and the maspin gene from the maternal DNA in the blood sample. In an exemplary embodiment, the amplification step is performed by PCR or methylation-specific PCR; in another exemplary embodiment, step (c) is performed by mass spectrometry, primer extension, polynucleotide hybridization, real-time PCR, or electrophoresis.

Furthermore, this invention relates to a method for detecting trisomy 18 in a fetus carried by a pregnant woman. The method includes the following steps: (a) obtaining a blood sample from the woman; (b) determining the methylation status of at least a portion of the maspin gene in the blood sample, wherein the portion of the maspin gene from the fetus and the portion from the woman are differentially methylated, thereby distinguishing the maspin gene from the woman and the maspin gene from the fetus in the blood sample; and (c) determining the levels of two different alleles of the fetal maspin gene, wherein a deviation of the ratio of the levels of the two alleles from 1:1 indicates trisomy 18 in the fetus. In some embodiments of this method, the two different alleles of the fetal maspin gene comprise a single nucleotide polymorphism (SNP). One exemplary SNP is located at 156 bp upstream from the transcription start site of the maspin gene.

BRIEF DESCRIPTION OF THE DRAWINGS

FIG. 2. Maspin promoter sequence after complete bisulfite conversion. The boxed sequence represents a fully methylated state at all CpG sites, which are numbered with respect to the transcription start site (+1). Bisulfite sequencing primers F and R are underlined with >>> and <<<, respectively. Methylation-specific PCR (MSP) primers are shown underneath. MF and MR are used for MMSP, which detects the methylated sequence, while UF and UR are for UMSP, which detects the unmethylated sequence. Artificial mismatches, shown in lowercase, were added to the $3^{rd}$ base from the 3' end of the primers to enhance specificity and sensitivity of the MSP assays. MP and UP are the TaqMan MGB (Minor Grove Binding) probes designed for the real-time quantitative MMSP and UMSP assays, respectively.

FIG. 5. Schematic diagram for detecting fetal trisomy 18 in maternal plasma. Closed and open circles represent methylated and unmethylated cytosines in CpG sites of the maspin promoter. The figures of 95% and 5% are merely for illustrative purposes only and represent one of the possible relative concentrations of fetal and maternal DNA in maternal plasma. Arrows represent UMSP primers that amplify only the unmethylated maspin (U-maspin) sequences of the fetus, but not the methylated maspin sequence of the mother. Hence, the allelic ratio of any single nucleotide polymorphism (SNP) within this region, in this case C/A, could be determined by analyzing the U-maspin PCR product. If this SNP is heterozygous for an euploid fetus, the allelic ratio will be 1:1. However, for a fetus with trisomy 18, the allelic ratio will deviate significantly from normal, and in one scenario may be 2:1. This U-maspin assay can thus be used for the non-invasive diagnosis of trisomy 18 by molecular analysis of the maternal plasma.

FIG. 6A-6D. Methylation status of CpG sites in the maspin promoter. Juxtaposed are data from placental tissues (FIG. 6A) and corresponding maternal buffy coat (FIG. 6B) from each of eight pregnancies in the first trimester (TP11, TP12, TP13, TP14, TP15, TP16, TP17, and TP21) and the same tissues (FIGS. 6C and 6D) from each of eight pregnancies in the third trimester (NP23, NP27, NP28, NP29, NP30, NP31, NP32, and NP40). Open and closed circles represent unmethylated and methylated cytosine residues, respectively. At least 9 randomly chosen clones, numbered in the column, were sequenced for each site of each tissue.

DEFINITIONS

Figure 1:
FIG. 1. Schematic representation of the maspin genomic sequence, including the promoter and exon 1. The position of 2 CpG islands are shown as solid black bars. Arrows marked "F" and "R" denote the location of the bisulfite sequencing primers used in our study. The genomic and exon sequences are derived from NT_025028 and NM_002639 (GenBank accession numbers). CpG sites are shown in small vertical bars underneath.

The term "pregnancy-associated disorder," as used in this application, refers to any condition or disease that may affect a pregnant woman, the fetus the woman is carrying, or both the woman and the fetus. Such a condition or disease may manifest its symptoms during a limited time period, e.g., during pregnancy or delivery, or may last the entire life span of the fetus following its birth. Some examples of a pregnancy-associated disorder include ectopic pregnancy, preeclampsia, preterm labor, and fetal chromosomal abnormalities such as trisomy 13, 18, or 21.

The term "epigenetic state" or "epigenetic status" as used herein refers to any structural feature at molecular level of a nucleic acid (e.g., DNA or RNA) other than the primary nucleotide sequence. For instance, the epigenetic state of a genomic DNA may include its secondary or tertiary structure determined or influenced by, e.g., its methylation pattern or its association with cellular proteins.

The term "methylation profile" or "methylation status," when used in this application to describe the state of methylation of a gene, refers to the characteristics of a DNA fragment relevant to methylation. Such characteristics include, but are not limited to, whether any of the cytosine (C) residues within this DNA sequence are methylated, location of methylated C residue(s), percentage of methylated C at any particular stretch of residues, and allelic differences in methylation due to, e.g., difference in the origin of the alleles or the level of gene expression.

The term "single nucleotide polymorphism" or "SNP" as used herein refers to the polynucleotide sequence variation present at a single nucleotide residue within different alleles of the same gene, e.g., the maspin gene. This variation may occur within the coding region or non-coding region (i.e., in the promoter region) of a gene. Detection of one or more SNP allows differentiation of different alleles of a single gene.

The term "blood" as used herein refers to a blood sample or preparation from a pregnant woman or a woman being tested for possible pregnancy. The term encompasses whole blood or any fractions of blood, such as serum and plasma as conventionally defined.

The term "bisulfite" as used herein encompasses all types of bisulfites, such as sodium bisulfite, that are capable of chemically converting a cytosine (C) to a uracil (U) without chemically modifying a methylated cytosine and therefore can be used to differentially modify a DNA sequence based on the methylation status of the DNA.

As used herein, a reagent that "differentially modifies" methylated or non-methylated DNA encompasses any reagent that modifies methylated and/or unmethylated DNA in a process through which distinguishable products result from methylated and non-methylated DNA, thereby allowing the identification of the DNA methylation status. Such processes may include, but are not limited to, chemical reactions (such as a C→U conversion by bisulfite) and enzymatic treatment (such as cleavage by a methylation-dependent endonuclease). Thus, an enzyme that preferentially cleaves methylated DNA is one capable of cleaving a DNA molecule at a much higher efficiency when the DNA is methylated, whereas an enzyme that preferentially cleaves unmethylated DNA exhibits a significantly higher efficiency when the DNA is not methylated.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260: 2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain; it includes regions preceding and following the coding region (leader and trailer) involved in the transcription/translation of the gene product and the regulation of the transcription/translation, as well as intervening sequences (introns) between individual coding segments (exons).

In this application, the terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

As used in this application, an "increase" or a "decrease" refers to a detectable positive or negative change in quantity from an established standard control. An increase is a positive change preferably at least 2-fold, more preferably at least 5-fold, and most preferably at least 10-fold of the control value. Similarly, a decrease is a negative change preferably at least 50%, more preferably at least 80%, and most preferably at least 90% of the control. Other terms indicating quantitative changes or differences from a comparative basis, such as "less," are used in this application in the same fashion as described above.

A "polynucleotide hybridization method" as used herein refers to a method for detecting the presence and/or quantity of a polynucleotide based on its ability to form Watson-Crick base-pairing, under appropriate hybridization conditions, with a polynucleotide probe of a known sequence. Examples of such hybridization methods include Southern blotting and Northern blotting.

"Primers" as used herein refer to oligonucleotides that can be used in an amplification method, such as a polymerase chain reaction (PCR), to amplify a nucleotide sequence based on the polynucleotide sequence corresponding to a gene of interest, e.g., the maspin gene in various methylation states. At least one of the PCR primers for amplification of a polynucleotide sequence is sequence-specific for the sequence.

"Standard control" as used herein refers to a sample comprising a gene of a predetermined amount or methylation profile (which may include multiple different and separable characteristics related to methylation) suitable for the use of a method of the present invention, in order for comparing the amount or methylation status of a particular gene, e.g., the maspin gene, that is present in a test sample. A sample serving as a standard control provides an average amount or methylation profile of a gene of interest that is typical for a defined time (e.g., first trimester) during pregnancy in the blood of an average, healthy pregnant woman carrying a normal fetus, both of who are not at risk of developing any pregnancy-associated disorders or complications.

The term "average," as used in the context of describing a pregnant woman who is healthy, carries a chromosomally normal fetus, does not and will not develop any pregnancy-associated conditions (such as ectopic pregnancy, preeclampsia, or preterm labor), refers to certain characteristics, such as the methylation profile of a particular gene (e.g., the maspin gene) of both maternal and fetal origins found in the woman's blood, that are representative of a randomly selected group of healthy women who are pregnant with chromosomally normal fetuses and not susceptible to any pregnancy-related diseases or conditions. This selected group should comprise a sufficient number of women such that the average amount or methylation profile of the gene of interest among these women reflects, with reasonable accuracy, the corresponding profile in the general population of healthy pregnant women with healthy fetuses. In addition, the selected group of women generally have a similar gestational age to that of a woman whose blood is tested for indication of a potential pregnancy-associated disorder. The preferred gestational age for practicing the present invention may vary depends on the disorder that is being screened for. For example, a pregnant woman is screened for the risk of preeclampsia preferably during the second trimester of the pregnancy, whereas fetal chromosomal aneuploidy is preferably screened for and diagnosed as early as possible. Moreover, the preferred gestational age for testing may also depend on the gene of interest in testing.

The term "preeclampsia" as used herein refers to a condition that occurs during pregnancy, the main symptom of which is various forms of high blood pressure often accompanied by the presence of proteins in the urine and edema (swelling). Preeclampsia, sometimes called toxemia of pregnancy, is related to a more serious disorder called "eclampsia," which is preeclampsia together with seizures. These conditions usually develop during the second half of pregnancy (after 20 weeks), though they may develop shortly after birth or before 20 weeks of pregnancy.

The term "preterm labor" or "premature labor" as used herein refers to the condition where labor that begins more than three weeks before the full gestation period of about 40 weeks, which often leads to premature birth if not treated.

The term "hyperemesis gravidarum" refers to extreme, persistent nausea and vomiting during pregnancy, particularly during the first trimester. The nausea and vomiting may lead to dehydration and prevent necessary weight gain for the pregnancy.

An "ectopic pregnancy" refers to an abnormal pregnancy in which a fertilized egg has implanted outside the uterus. Although in most cases of ectopic pregnancy the egg settles in the fallopian tubes, this term also encompasses abnormal pregnancies where the fertilized egg is implanted in a woman's ovary, abdomen, or cervix.

DETAILED DESCRIPTION OF THE INVENTION

I. Introduction

The presence of fetal DNA in maternal plasma was first reported in 1997 and offers the possibility for non-invasive prenatal diagnosis simply through the analysis of a maternal blood sample (Lo et al., Lancet 350:485-487, 1997). To date, numerous potential clinical applications have been developed. In particular, quantitative abnormalities of fetal DNA concentrations in maternal plasma have been found to be associated with a number of pregnancy-associated disorders, including preeclampsia, preterm labor, antepartum hemorrhage, invasive placentation, fetal Down syndrome, and other fetal chromosomal aneuploidies. Hence, fetal DNA analysis in maternal plasma has been suggested as a potential marker for the monitoring of fetomaternal well-being.

However, fetal DNA co-exists with background maternal DNA in maternal plasma. Hence, most reported applications have relied on the detection of Y-chromosome sequences as these are most conveniently distinguishable from maternal DNA. However, such an approach limits the applicability of the existing assays to only 50% of all pregnancies with male fetuses. Thus, there is much need for the development of gender-independent fetal DNA markers for maternal plasma detection.

It was previously demonstrated that fetal and maternal DNA can be distinguished by their differences in methylation status (U.S. Patent Application Publication No. 20030044388). Methylation is an epigenetic phenomenon, which refers to processes that alter a phenotype without involving changes in the DNA sequence. By exploiting the difference in the DNA methylation status between the paternally- and maternally-inherited alleles at H19, a locus exhibiting genomic imprinting (differential methylation and hence differential expression of two alleles of a single gene, related to the parental origin of a particular allele), one (Y.M.D. Lo) of the present inventors and his group first demonstrated the feasibility of using epigenetic markers to detect fetal-derived maternally-inherited DNA sequence from maternal plasma (Poon et al., Clin. Chem. 48:35-41, 2002). Landes et al. have also proposed the use of epigenetic markers for non-invasive prenatal diagnosis (U.S. Patent Application Publication No. 20030211522).

The present inventors have recently demonstrated that placenta-derived RNA can be detected in maternal plasma (Ng et al., Proc. Natl. Acad. Sci. USA 100:4748-4753, 2003). On the other hand, it has been shown that plasma DNA in normal individuals is predominantly derived from hematopoietic cells (Lui et al., Clin. Chem. 48:421-427, 2002). Thus, it has been hypothesized that the predominant source of maternal DNA is derived from peripheral blood cells while the placenta is a possible source of fetal DNA release into maternal plasma. Hence, one strategy for the development of a generic fetal-specific DNA marker for detection in maternal plasma is to identify a gene that is differentially methylated between the placenta and the maternal peripheral blood cells.

Maspin (mammary serine protease inhibitor) is a protein belonging to the family of serine protease inhibitors. It is found to be expressed in a variety of normal tissues, mainly those of epithelial origin, such as breast, prostate, placenta, testis, colon and the small intestines. The clinical significance of maspin was realized when a study by Zou et al. (Science 263:526-529, 1994) demonstrated its reduced expression in human breast carcinoma cells. Subsequent studies noted an inverse relationship between its expression and cancer prognosis or the presence of metastasis. To date, the maspin gene is widely accepted as a tumor suppressor gene, whose physiological function lies in the promotion of cell-matrix adhesion and the inhibition of cell invasion. Investigations fail to reveal DNA mutations that are responsible for the altered expression of maspin in tumors. Instead, maspin was found to be under epigenetic control where expression is suppressed by promoter methylation and histone deacetylation (Futscher et al., Nat. Genet. 31:175-179, 2002; Maass et al., Biochem. Biophys. Res. Commun. 297:125-128, 2002). Futscher et al., supra, observed that the 19 CpG sites spanning the maspin promoter were uniformly unmethylated in maspin-positive cell types, while they were densely methylated in all maspin-negative cell types.

The present inventors demonstrated, for the first time, that the maspin gene is differentially methylated between the fetal DNA from the fetus (e.g., from the placenta) and the maternal DNA from the mother's peripheral blood cells. This discovery thus provides a new approach for distinguishing fetal and maternal DNA and new methods for non-invasive prenatal diagnosis.

II. General Methodology

Practicing this invention utilizes routine techniques in the field of molecular biology. Basic texts disclosing the general methods of use in this invention include Sambrook and Russell, Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, *Tetrahedron Lett.* 22: 1859-1862 (1981), using an automated synthesizer, as described in Van Devanter et. al., *Nucleic Acids Res.* 12: 6159-6168 (1984). Purification of oligonucleotides is performed using any art-recognized strategy, e.g., native acrylamide gel electrophoresis or anion-exchange high performance liquid chromatography (HPLC) as described in Pearson & Reanier, *J. Chrom.* 255: 137-149 (1983).

The sequence of the maspin gene, a polynucleotide encoding the Maspin polypeptide, and synthetic oligonucleotides can be verified using, e.g., the chain termination method for sequencing double-stranded templates of Wallace et al., *Gene* 16: 21-26 (1981).

III. Acquisition of Blood Samples and Extraction of DNA

The present invention relates to analyzing the epigenetic status of fetal DNA found in maternal blood as a non-invasive means to detect the presence and/or to monitor the progress of a pregnancy-associated condition or disorder. Thus, the first steps of practicing this invention are to obtain a blood sample from a pregnant woman and extract DNA from the sample.

A. Acquisition of Blood Samples

A blood sample is obtained from a pregnant woman at a gestational age suitable for testing using a method of the present invention. The suitable gestational age may vary depending on the disorder tested, as discussed below. Collection of blood from a woman is performed in accordance with the standard protocol hospitals or clinics generally follow. An appropriate amount of peripheral blood, e.g., typically between 5-50 ml, is collected and maybe stored according to standard procedure prior to further preparation.

B. Preparation of Blood Samples

The analysis of fetal DNA found in maternal blood according to the present invention may be performed using, e.g., the whole blood, serum, or plasma. The methods for preparing serum or plasma from maternal blood are well known among those of skill in the art. For example, a pregnant woman's blood can be placed in a tube containing EDTA or a specialized commercial product such as Vacutainer SST (Becton Dickinson, Franklin Lakes, N.J.) to prevent blood clotting, and plasma can then be obtained from whole blood through centrifugation. On the other hand, serum may be obtained with or without centrifugation following blood clotting. If centrifugation is used then it is typically, though not exclusively, conducted at an appropriate speed, e.g., 1,500-3,000×g. Plasma or serum may be subjected to additional centrifugation steps before being transferred to a fresh tube for DNA extraction.

In addition to the acellular portion of the whole blood, DNA may also be recovered from the cellular fraction, enriched in the buffy coat portion, which can be obtained following centrifugation of a whole blood sample from the woman and removal of the plasma.

C. Extraction of DNA

There are numerous known methods for extracting DNA from a biological sample including blood. The general methods of DNA preparation (e.g., described by Sambrook and Russell, *Molecular Cloning: A Laboratory Manual* 3d ed., 2001) can be followed; various commercially available reagents or kits, such as QiaAmp DNA Mini Kit or QiaAmp DNA Blood Mini Kit (Qiagen, Hilden, Germany), Genom-icPrep™ Blood DNA Isolation Kit (Promega, Madison, Wis.), and GFX™ Genomic Blood DNA Purification Kit (Amersham, Piscataway, N.J.), may also be used to obtain DNA from a blood sample from a pregnant woman. Combinations of more than one of these methods may also be used.

IV. Methylation-Specific Chemical Modification of DNA

Upon being extracted from a blood sample of a pregnant woman, the DNA is treated with a reagent capable of chemically modifying DNA in a methylation differential manner, i.e., different and distinguishable chemical structures will result from a methylated cytosine (C) residue and an unmethylated C residue following the treatment. Typically, such a reagent reacts with the unmethylated C residue(s) in a DNA molecule and converts each unmethylated C residue to a uracil (U) residue, whereas the methylated C residues remain unchanged. This C→U conversion allows detection and comparison of methylation status based on changes in the primary sequence of the nucleic acid. An exemplary reagent suitable for this purpose is bisulfite, such as sodium bisulfite. Methods for using bisulfite for chemical modification of DNA are well known in the art (see, e.g., Herman et al., *Proc. Natl. Acad. Sci. USA* 93:9821-9826, 1996) and will not be discussed in detail here.

As a skilled artisan will recognize, any other reagents that are unnamed here but have the same property of chemically (or through any other mechanism) modifying methylated and unmethylated DNA differentially can be used for practicing the present invention. For instance, methylation-specific modification of DNA may also be accomplished by methylation-sensitive restriction enzymes, some of which typically cleave an unmethylated DNA fragment but not a methylated DNA fragment, while others (e.g., methylation-dependent endonuclease McrBC) cleave DNA containing methylated cytosines but not unmethylated DNA. In addition, a combination of chemical modification and restriction enzyme treatment, e.g., combined bisulfite restriction analysis (COBRA), may be used for practicing the present invention.

V. Polynucleotide Sequence Amplification and Determination

Following the chemical modification of DNA in a methylation-differential manner, the treated DNA is then subjected to sequence-based analysis, such that the maspin gene from the fetal DNA may be distinguished from the maspin gene from the maternal DNA, and that fetal maspin gene methylation profile may be determined and compared to a standard control.

A. Amplification of Nucleotide Sequences

An amplification reaction is optional prior to the maspin gene sequence analysis after methylation specific modification. In some embodiments of this invention, the amplification is performed to preferentially amplify a portion of the maspin gene that has a particular methylation pattern, such that only the maspin gene from one particular source, e.g., from the placenta or other tissues of the fetus, is detected and analyzed.

A variety of polynucleotide amplification methods are well established and frequently used in research. For instance, the general methods of polymerase chain reaction (PCR) for polynucleotide sequence amplification are well known in the art and are thus not described in detail herein.

For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available.

Although PCR amplification of a target polynucleotide sequence (e.g., a portion of the maspin gene where the fetal and maternal sequence is differentially methylated) is typically used in practicing the present invention, one of skill in the art will recognize that the amplification of a maspin gene sequence found in a maternal blood sample may be accomplished by any known method, such as ligase chain reaction (LCR), transcription-mediated amplification, and self-sustained sequence replication or nucleic acid sequence-based amplification (NASBA), each of which provides sufficient amplification. More recently developed branched-DNA technology may also be used to qualitatively demonstrate the presence of a particular maspin gene sequence (which represents a particular methylation pattern), or to quantitatively determine the amount of a particular maspin gene sequence (which represents a particular methylation pattern) in the maternal blood. For a review of branched-DNA signal amplification for direct quantitation of nucleic acid sequences in clinical samples, see Nolte, *Adv. Clin. Chem.* 33:201-235, 1998.

B. Determination of Polynucleotide Sequences

Techniques for polynucleotide sequence determination are also well established and widely practiced in the relevant research field. For instance, the basic principles and general techniques for polynucleotide sequencing are described in various research reports and treatises on molecular biology and recombinant genetics, such as Wallace et al., supra; Sambrook and Russell, supra, and Ausubel et al., supra. DNA sequencing methods routinely practiced in research laboratories, either manual or automated, can be used for practicing the present invention. Additional means suitable for detecting changes (e.g., C→U) in a polynucleotide sequence for practicing the methods of the present invention include but are not limited to mass spectrometry, primer extension, polynucleotide hybridization, real-time PCR, and electrophoresis.

VI. Establishing a Standard Control

In order to establish a standard control for practicing the method of this invention, a group of healthy pregnant women carrying healthy fetuses are first selected. These women are of similar gestational age, which is within the appropriate time period of pregnancy for screening of conditions such as preeclampsia, fetal chromosomal aneuploidy, and preterm labor using the methods of the present invention. Similarly, a standard control is established using samples from a group of healthy non-pregnant women.

The healthy status of the selected pregnant women and the fetuses they are carrying are confirmed by well established, routinely employed methods including but not limited to monitoring blood pressure of the women, recording the onset of labor, and conducting fetal genetic analysis using CVS and amniocentesis.

Furthermore, the selected group of healthy pregnant women carrying healthy fetuses must be of a reasonable size, such that the average amount of fetal maspin gene in the maternal blood or the methylation profile of at least a portion of the fetal maspin gene in the maternal blood obtained from the group can be reasonably regarded as representative of the normal or average amount or methylation profile among the general population of healthy women carrying healthy fetuses. Preferably, the selected group comprises at least 10 women.

A standard control for fetal maspin gene methylation profile may reflect multiple different and separable aspects of the methylation status of this gene. For example, one aspect of a methylation profile is whether the C residue is methylated or not; another aspect is the number of methylated C bases within a particular region of the maspin gene; a further aspect of the profile is the percentage(s) of methylated C at any given locations. Additional aspects of a methylation profile may include, but are not limited to, the allelic difference in methylation, the ratio of differentially methylated alleles, and the like. Fetal maspin gene methylation profile may also vary depending on the tissue type, e.g., placental or other fetal tissue. Thus, separate standard controls may be established for different fetal tissues used in testing.

Once an average level or methylation profile is established for the fetal maspin gene present in the maternal blood based on the individual values found in each woman of the selected healthy control group, this average or median or representative value or profile is considered a standard control. Any blood sample that contains a similar amount of the fetal maspin gene or a similar methylation profile of the fetal maspin gene can thus be used as a standard control. Furthermore, a solution containing maspin DNA in the average or median or representative amount or of the average or median or representative methylation profile can also be artificially assembled and serve as a standard control. In addition, separate standard controls may also be established for different aspects of the methylation profile of the maspin gene.

EXAMPLES

The following examples are provided by way of illustration only and not by way of limitation. Those of skill in the art will readily recognize a variety of non-critical parameters that could be changed or modified to yield essentially similar results.

The objectives of this study are:
(1) To systematically compare the methylation status of the maspin gene between placental tissue and maternal peripheral blood cells;
(2) To develop an epigenetic assay for specific detection and quantification of placenta-derived maspin DNA in maternal plasma.
(3) To study the quantitative profile of placenta-derived maspin DNA concentration in maternal plasma during the course of normal pregnancy; and
(4) To study the presence of quantitative aberrations in the concentration of placenta-derived maspin DNA in maternal plasma in pregnancy-associated conditions, such as, but not limited to preeclampsia.
(5) To develop a method for the detection of trisomy 18 in a fetus in a pregnant woman by determining the ratio of different alleles of placenta-derived maspin.

MATERIALS AND METHODS

1. To Systematically Compare the Methylation Status of the Maspin Gene Between Placental Tissues and Maternal Peripheral Blood Cells To demonstrate that difference does exist between the methylation status of the maspin gene in the placenta and maternal blood, the present inventors performed bisulfite sequencing on DNA extracted from 8 paired placental tissue and maternal peripheral venous blood from the third trimester (38-39 weeks, median 38.5 weeks, SD 0.52 weeks) of pregnancy. In addition, for the purpose of prenatal monitoring, it would be beneficial if the marker is detectable as early as possible during pregnancy. Hence, bisulfite sequencing was also performed on DNA extracted from 8 paired chorionic villus samples (CVS) and maternal blood from the first trimester (9-13 weeks, median 10.5 weeks, SD 1.22 weeks) of pregnancy. To demonstrate that this difference in the methylation status of the maspin gene is independent of the fetal sex, the inventors included both male (TP12, TP14, TP15, TP17, NP27, NP28, NP29, NP30, NP31, NP40) and female fetuses (TP11, TP13, TP16, TP21, NP23, NP32) for this part of the study.

Sample Collection and Processing.

The tissues of first and third trimesters were obtained respectively from pregnant subjects attending clinic for prenatal diagnosis by chorionic villus sampling and from those requiring delivery by elective cesarean section at term. Six milliliters of the blood samples were collected in EDTA tubes and were centrifuged at 1600×g for 10 min at 4° C. Plasma was carefully transferred into plain polypropylene tubes for re-centrifugation at 16000×g for 10 min at 4° C., and stored in fresh plain tubes without any cell pellet. The buffy coat portion was obtained after careful removal of plasma and stored separately at −20° C. Chorionic villus biopsy and placenta after delivery were rinsed in phosphate buffered saline and stored in plain polypropylene tubes at −80° C.

Bisulfite Sequencing.

DNA was extracted from the placental tissues and maternal buffy coat by using the QiaAmp DNA Mini Kit and QiaAmp DNA Blood Mini Kit (Qiagen, Hilden, Germany) respectively according to the manufacturer's instructions. For each sample, 1 µg DNA was subjected to bisulfite conversion, which converts unmethylated cytosine residues to uracil but leaves methylated cytosine residues unchanged, by the CpGenome DNA Modification Kit (Intergen, Burlington, Mass.) according to manufacturer's instructions. The bisulfite converted DNA was then subjected to PCR amplification with primers F and R (FIGS. 1 and 2) flanking the CpG sites, which may contain methylated cytosine residues, in the converted maspin promoter. These primers were designed not to bind to any potentially methylated cytosine residues. These primers are shown by way of illustration and should not be seen to limit the range of primers which can be used for this purpose. Reagents supplied in the TaqMan PCR Core Reagents Kit (Applied Biosystems, Foster City, Calif.) were used. In a final reaction volume of 50 µl, 1× Buffer II, 4 mM $MgCl_2$, 160 µM of each dNTP, 300 nM of each primer, 3% dimethylsulfoxide (DMSO), and 3U Taq-Gold polymerase were mixed. The thermal profile consisted of an initial denaturation step of 95° C. for 10 min followed by 40 cycles of 95° C. for 1 min, 60° C. for 1 min, 72° C. for 1 min, and a final extension of 72° C. for 10 min. To analyze methylation status at the resolution of a single molecule, the PCR product was TA-cloned into a plasmid vector using the pGEM-T Easy Vector System (Promega, Madison, Wis.) and the inserts from at least 10 positive recombinant clones were analyzed by cycle sequencing using the BigDye Terminator Cycle Sequencing v1.1 kit (Applied Biosystems) as per the manufacturer's instructions. After purification by genCLEAN columns (Genetix), 8 µl of the samples were added to 12 µl of Hi-Di formamide and run on a 3100 DNA Analyzer (Applied Biosystems).

Data Comparison and Statistical Analysis.

A CpG site was scored as methylated if the sequence was cytosine; scored as unmethylated if it was occupied by a thymine residue (deoxy counterpart of uracil). The proportion of methylated cytosine residue for each CpG site in each type of tissues was determined for each pregnancy. The distribution of methylated and unmethylated cytosines were compared between the placental tissues and maternal buffy coat for each CpG site (FIG. 3). Statistical analysis was performed using the Sigma Stat 3.0 software (SPSS).

2. To Develop an Epigenetic Assay for the Specific Detection and Quantification of Placenta-Derived Maspin DNA in Maternal Plasma Fetal DNA coexists with a background of maternal DNA in plasma of pregnant women. As demonstrated previously, plasma DNA is predominantly derived from blood cells in normal, non-pregnant subjects. Based on this, it is hypothesized that maternal DNA in maternal plasma is also predominantly derived from maternal blood cells in which the maspin promoter is densely methylated. On the other hand, another study has shown that fetal RNA detected in maternal plasma is derived from the placenta. In light of this finding, it is hypothesized that the contribution of fetal DNA in maternal plasma may also originate from the placenta and hence possess the same methylation status in the maspin promoter as that of the placenta. To test whether the maspin promoter in placenta may be unmethylated, which would be different from the background of methylated maspin promoter of the maternal origin, it was examined if this epigenetic difference would allow fetal-specific detection of placenta-derived maspin DNA in maternal plasma. It was examined whether unmethylated maspin sequences would:
(a) be detectable in plasma of pregnant women;
(b) increase in concentration as pregnancy progresses; and
(c) decrease substantially in concentration in maternal plasma after delivery of the fetus.

Methylation-Specific PCR Primer Design.

Based on the methylation map generated from study (1) above, primers that discriminate between the unmethylated and methylated versions of the maspin promoter were designed, based on the principles of methylation-specific PCR (MSP) (Herman et al., *Proc. Natl. Acad. Sci. USA* 93:9821-9826, 1996). The assays specific for the unmethylated maspin (U-maspin) and methylated maspin (M-maspin) promoters were designated as UMSP and MMSP, respectively. The primers for UMSP (UF and UR) and for MMSP (MF and MP) are shown in FIG. 2. We employed the double Amplification Refractory Mutation System approach, which involves the use of two allele-specific primers simultaneously during PCR when there is a need to distinguish a sequence of interest from two or more closely related sequences. To enhance the specificity of the primers, an additional mismatch (shown as lower case in primer sequences of FIG. 2) was introduced into the third base from the 3' end of both primers.

Real-time quantitative methylation-specific PCR. Two dual labeled fluorescent TaqMan MGB probes, MP and UP were designed to adopt the UMSP and MMSP respectively into the real-time quantitative assays. Their sequences are shown in FIG. 2. Calibration curves were prepared by serial dilutions of high performance liquid chromatography-purified single stranded synthetic DNA oligonucleotides (Genset Oligos, Singapore) specific for the respective amplicons, with concentrations ranging from $1 \times 10^7$ copies to 5 copies. Quantitative MSP data were expressed as copies of unmethylated or methylated DNA per milliliter of plasma. The detectability of the unmethylated maspin promoter sequence (U-maspin) in maternal plasma collected from normal pregnancies during the third trimester, just before elective cesarean section and after delivery of the fetus, and also during all three trimesters of pregnancy were determined using the UMSP quantitative assay. As blood cells have methylated maspin promoter, it is expected that the MSP system for methylated maspin sequence (i.e., the MMSP system) would give a positive result in all plasma samples, whether from pregnant or non-pregnant individuals. Thus, the MMSP assay in the real-time quantitative PCR format was used as a positive control.

3. To Study the Quantitative Profile of Placenta-Derived Maspin DNA Concentration in Maternal Plasma During the Course of Normal Pregnancy The quantitative profile of U-maspin during normal pregnancy has been investigated. Six milliliters of maternal blood from women in the first, second and third trimesters of pregnancies were collected for quantification. For the third trimester pregnancies, women who underwent elective cesarean section were recruited. Blood was collected before delivery and at 24 hours after delivery. The concentration of the U-maspin DNA was determined in these maternal plasma samples. SRY quantification (Lo et al., *Am. J. Hum. Genet.* 64:218-224, 1998) was also performed for samples collected from male-carrying pregnancies. Correlation between the U-maspin and SRY quantitative data was determined.

4. Placenta-Derived Maspin DNA in Maternal Plasma and Serum as a Marker for Pregnancy Complications Quantitative aberrations of fetal DNA concentrations in maternal plasma and serum have been associated with a number of pregnancy-associated disorders. Placenta-derived maspin DNA can therefore be used as a marker for predicting, detecting, diagnosing and monitoring pregnancy-associated disorders, including, but not limited to preeclampsia, preterm labor, hyperemesis gravidarum, ectopic pregnancies, molar pregnancies, intrauterine growth retardation and chromosomal aneuploidies, such as fetal Down syndrome, fetal trisomy 18, fetal trisomy 13. Maternal plasma U-maspin concentration was determined by the real-time quantitative assay among 8 preeclamptic pregnant women bearing fetuses of both sexes (median gestational age: 36.1 weeks) and from 16 gestational age matched pregnant women without preeclampsia as controls (median gestational age: 36 weeks).

5. Development of a Method for the Detection of Trisomy 18 in a Fetus in a Pregnant Woman by Determining the Ratio of Different Alleles of Placenta-Derived Maspin.

Primer Extension Reaction for Genotypic Analysis of U-Maspin.

Genotypic analysis of a single nucleotide polymorphism (SNP) positioned at 156 bp upstream of the transcription start site in the maspin promoter was performed on placental tissues, maternal blood cells and plasma collected from eight fetomaternal pairs. SNP genotyping was performed on genomic DNA from the placental tissues and maternal blood cells using the standard primer extension (homogenous MassEXTEND (hME)) protocol on a MassARRAY system (SEQUENOM, San Diego, Calif.), which is a matrix-assisted laser desorption ionization/time-of-flight (MALDI-TOF) MS system (Tang et al., *Proc. Natl. Acad. Sci. USA* 96:10016-20, 1999).

Figure 4:
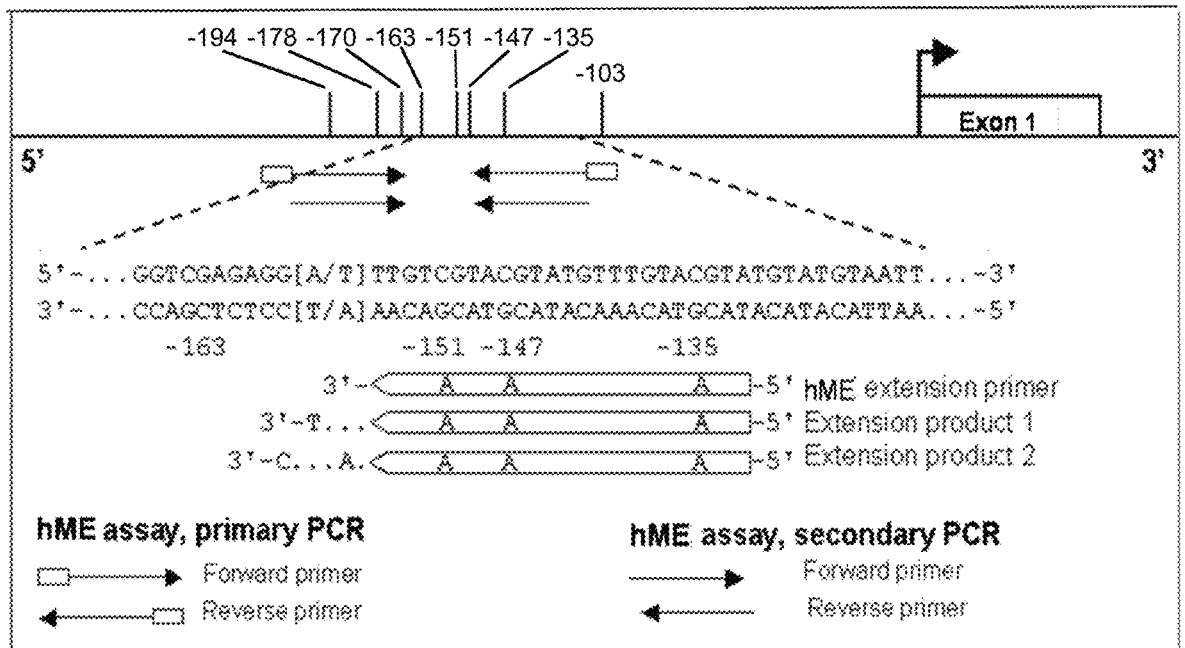
FIG. 4. Schematic diagram depicting the design for the U-maspin MassEXTEND reaction. The location of the −156 SNP is indicated in square brackets. The A/C SNP when bisulfite converted and interrogated in the reverse sense becomes a T/A SNP. The nested primers for the U-maspin MassEXTEND reaction (line arrows) are indicated schematically. Nucleotide positions on the extension primer which correspond to the unmethylated CpG sites are indicated by the positions marked "A" (adenine). hME: homogenous MassEXTEND.

A method for determining the −156 SNP genotype among the U-maspin sequences in maternal plasma was then developed. 0.8 mL of plasma was bisulfite converted as described above. The maspin promoter was amplified using nested primers, shown as hME primary and secondary primers in FIG. 4, by conventional PCR. MassEXTEND assay was performed according to manufacturer's instructions. The nested primers and extension primer were designed to anneal to U-maspin promoter sequences (FIG. 4). The extension reaction was performed using a terminator mix consisted of ddCTP, ddGTP, ddTTP and dATP. The extension reaction begins at the SNP site (FIG. 4).

Gene Dosage Assessment of Fetal Chromosome 18.

Genotyping of the −156 SNP was first performed on genomic DNA extracted from placental tissues collected from both normal and pregnancies involving a fetus with trisomy 18. Cases heterozygous for the −156 SNP were identified. DNA extracted from the placental tissues of these cases were bisulfite converted and U-maspin was amplified using the nested conventional PCR as described above. The MassEXTEND assay targeting the −156 U-maspin SNP alleles as described above was then applied to the PCR products. The abundance of the two U-maspin alleles at the −156 SNP was determined by comparing the respective peak areas for each allele as shown by the mass spectra determined by the MassARRAY system. As maspin is located on chromosome 18 and U-maspin is derived from the placenta, the relative abundance of the two U-maspin alleles is reflective of the number of fetal chromosome 18 (FIG. 5). The reliability of the assay and allelic ratio determination was assessed by testing two sample mixtures comprised of 95% DNA from a maternal blood cell sample and 5% DNA from the corresponding placental tissue obtained from a pregnancy involving a karyotypically normal fetus.

RESULTS AND DISCUSSION

Figure 3A:
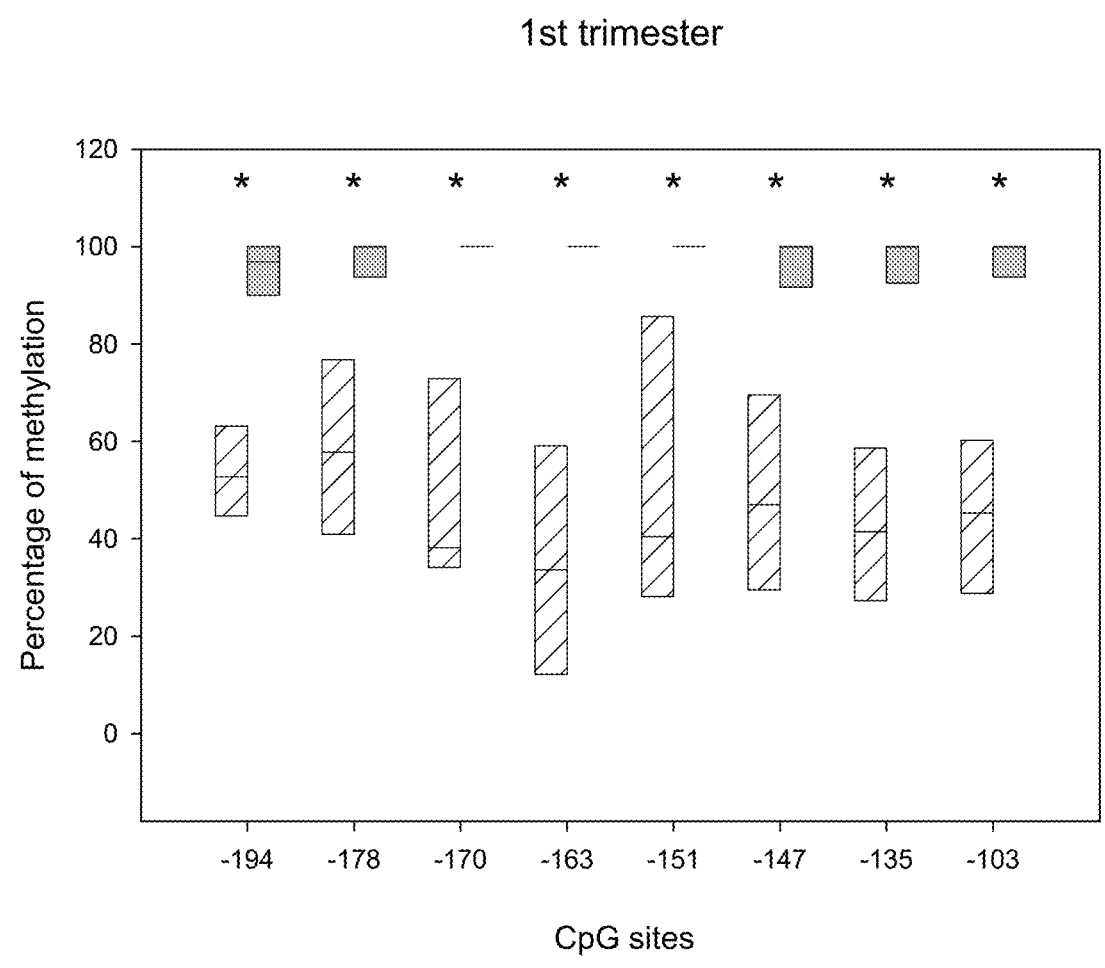
FIGS. 3A-3B. Percentage of methylation of cytosine residues in CpG sites of the maspin promoter. Data are shown for the paired placental tissue and maternal buffy coat from 8 first trimester pregnancies (FIG. 3A), and 8 third trimester pregnancies (FIG. 3B). The lines inside the boxes denote the medians. The boxes mark the interval between the 25th and 75th percentiles.
Figure 3B:
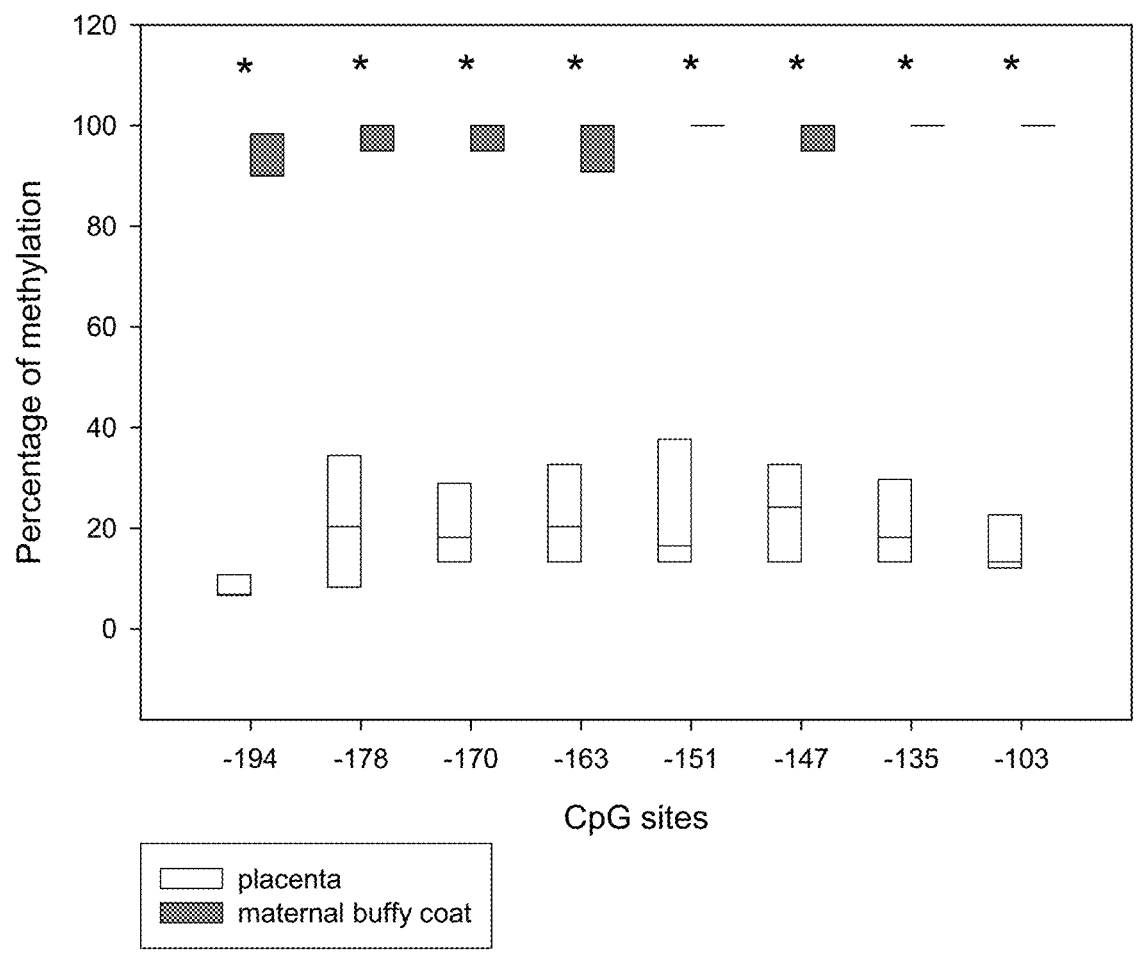

Comparison of Methyation Status of the Maspin Promoter Between Placental Tissue and Maternal Peripheral Blood Cells Bisulfite sequencing of paired tissues from the first and third trimesters revealed that most of the CpG sites in the maspin promoter of maternal buffy coat DNA was predominately methylated, while that in the placental tissue DNA was relatively unmethylated (FIGS. 6A, 6B, 6C, and 6D). For both trimesters, all of these eight CpG sites, located 194 to 103 base pairs upstream of the transcriptional start, were demethylated in the placental tissue, relative to the maternal buffy coat, to a statistically significant extent (Chi-square, $P<0.0001$; FIGS. 3A and 3B). Hence, these results have verified the hypothesis that placental tissue that expresses maspin indeed has an unmethylated promoter. This phenomenon is observed as early as the 10th week of gestation and thus makes early detection of U-maspin possible.

There is no sign of genomic imprinting in the loci investigated for both type of tissues. However, in the placental tissue, some degree of microheterogeneity was observed in the methylation profile. This could be attributed to the mixed cell types found in the placental tissue being used.

Specific Detection of Placenta-Derived Maspin DNA in Maternal Plasma

As proven by the bisulfite sequencing data, an epigenetic difference does exist between the placental tissue and the maternal peripheral blood cells, and thus can be exploited to develop PCR assays for specific detection. There are several criteria for choosing these pairs of primers. First, it is necessary to design a reasonably short (<120 bp) amplicon, in order to optimize for sensitivity, especially when bisulfite conversion destroys most of the DNA. Second, it is necessary to have an amplicon long enough for placing the flourescent probe. MGB probe was designed, since it requires a shorter probe DNA sequence. In the case of the present inventors, primers flanking CpG sites −170 and −147 are chosen, which give an amplicon of 89 base pairs for MMSP and 98 base pairs for UMSP (FIG. 2).

Figure 7:
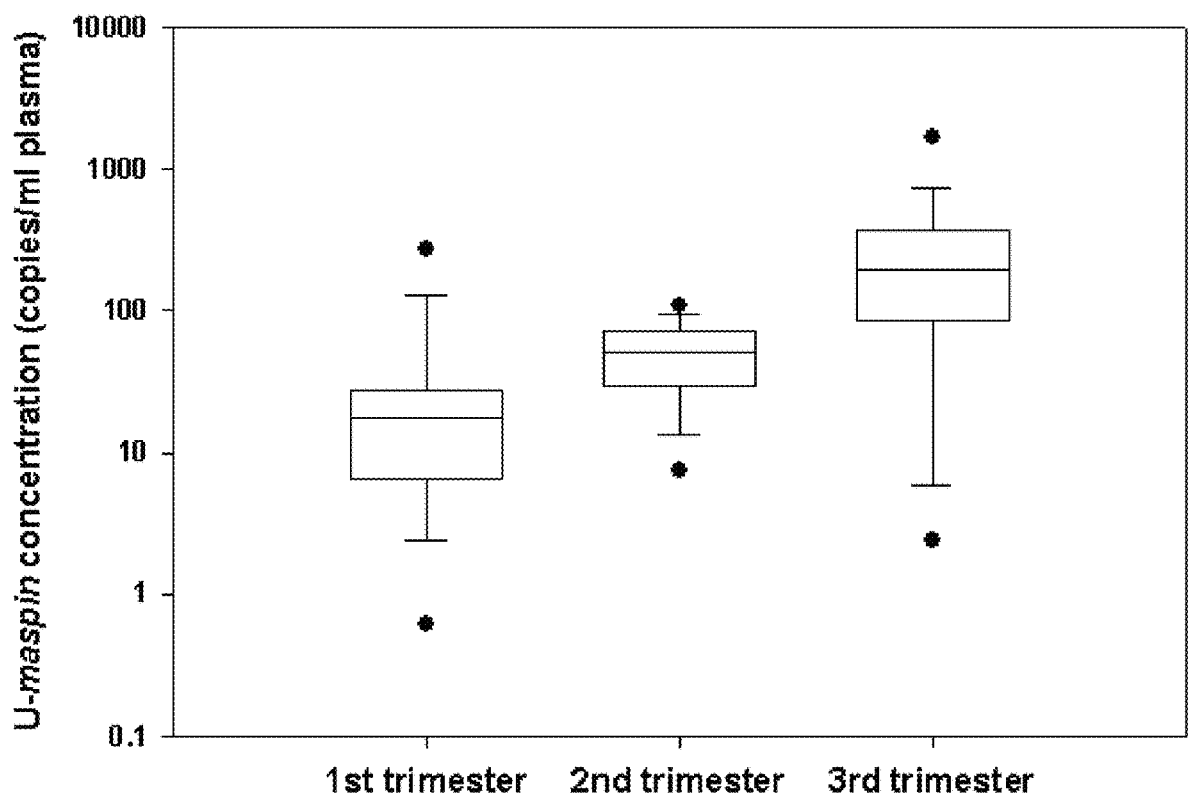
FIG. 7. Box plots of U-maspin concentrations in first-, second- and third-trimester maternal plasma. Line within each box denotes the median. Limits of the box denote the $25^{th}$ and $75^{th}$ percentiles. Whiskers denote the $5^{th}$ and $95^{th}$ percentiles. Filled circles depict the outliers.

U-maspin was detected in all the 8 samples of maternal plasma obtained from third trimester and all the 15 samples of maternal plasma obtained from third trimester, the 10 samples from second trimester and the 11 samples from first trimester (FIG. 7). This demonstrated that U-maspin could be readily detected in pregnancies, as early as the 10th week of gestation, despite the placental tissue is only partially demethylated at this time.

Figure 8:
FIG. 8. U-maspin concentration in maternal plasma before and 24 hours after delivery. Paired samples from the same pregnancy are depicted by identical symbols connected by a line.

After delivery of the fetus, the concentration of U-maspin in maternal plasma decreased almost to an undetectable level for all 6 pregnancies requiring cesarean section (FIG. 8). This result illustrated that U-maspin in maternal plasma was predominantly derived from the fetus. Thus, U-maspin behaves similarly as the established fetal DNA marker, SRY (present on the Y chromosome), in maternal plasma, which also clears after delivery of the fetus.

Figure 9:
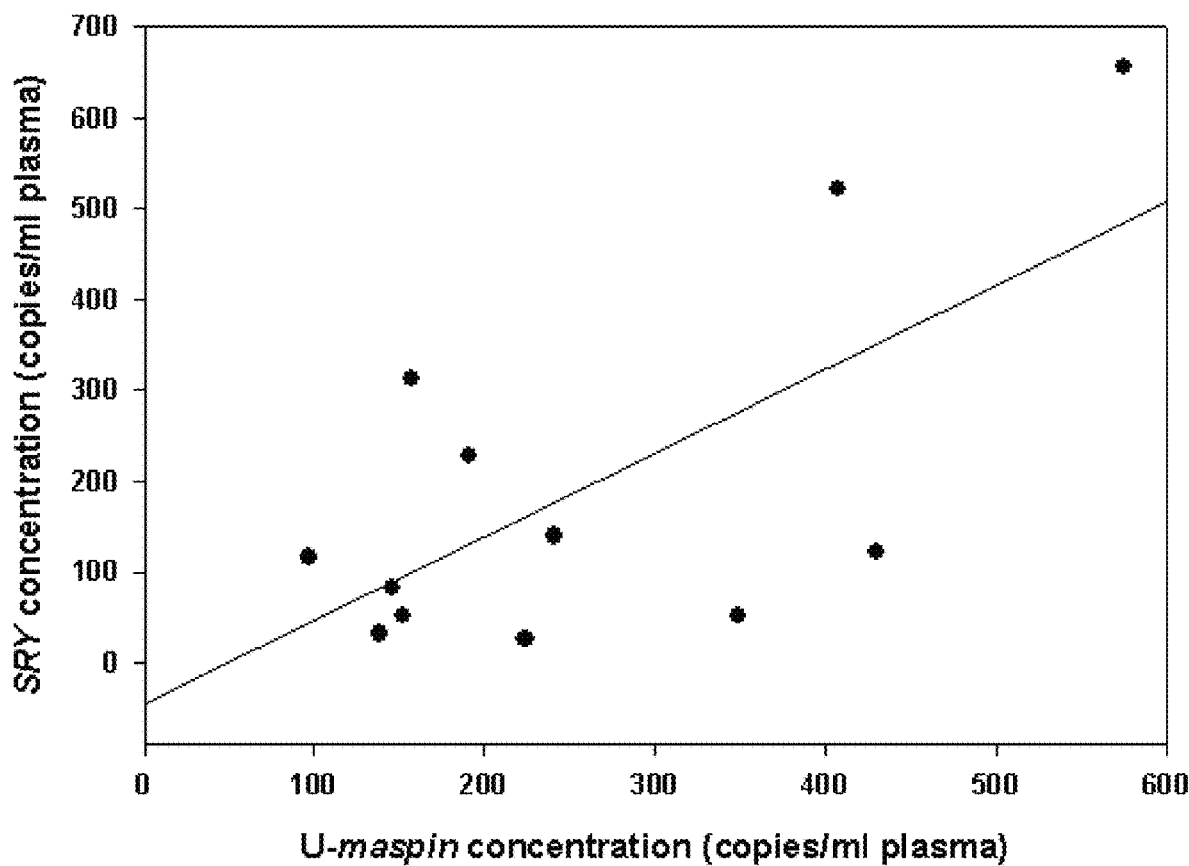
FIG. 9. Correlation between U-maspin and SRY concentrations in maternal plasma.

U-maspin and bisulfate-converted SRY concentrations were positively correlated (Pearson correlation, correlation coefficient, r=0.668 and P=0.02) in the plasma from 12 pregnant women bearing male fetuses (FIG. 9).

Elevated Maternal Plasma U-Maspin Concentration in Preeclampsia.

Figure 10:
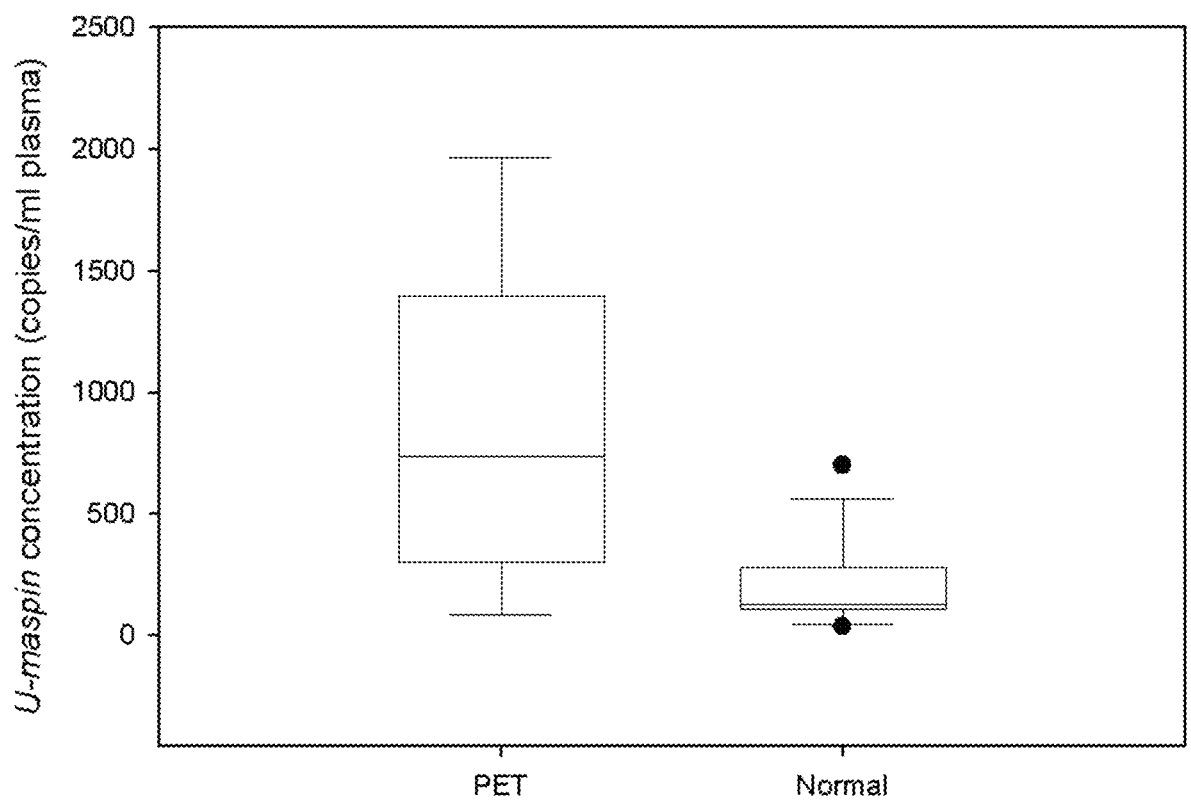
FIG. 10. U-maspin concentrations in maternal plasma of women with preeclamptic (PET) and healthy (Normal) pregnancies. Line within each box denotes the median. Limits of the box denote the $25^{th}$ and $75^{th}$ percentiles. Whiskers denote the $5^{th}$ and $95^{th}$ percentiles. Filled circles depict the outliers.

U-maspin DNA concentration was measured in the plasma obtained from 8 preeclamptic pregnant women and 16 gestational age matched pregnant women without preeclampsia as controls. The median U-maspin concentration in maternal plasma was 5.7-fold elevated in the preeclamptic group (median 737.7 copies/mL, IQR 306.9-1397.0) relative to the control group (median 130.3 copies/mL, IQR 110.7-286.2) (FIG. 10). A statistically significant difference in the maternal plasma U-maspin concentrations between the preeclamptic and control groups was observed (LogXact logistic regression by matched case-control analysis, P=0.01158).

Detection of Placenta-Derived U-Maspin in Maternal Plasma.

Figure 11:
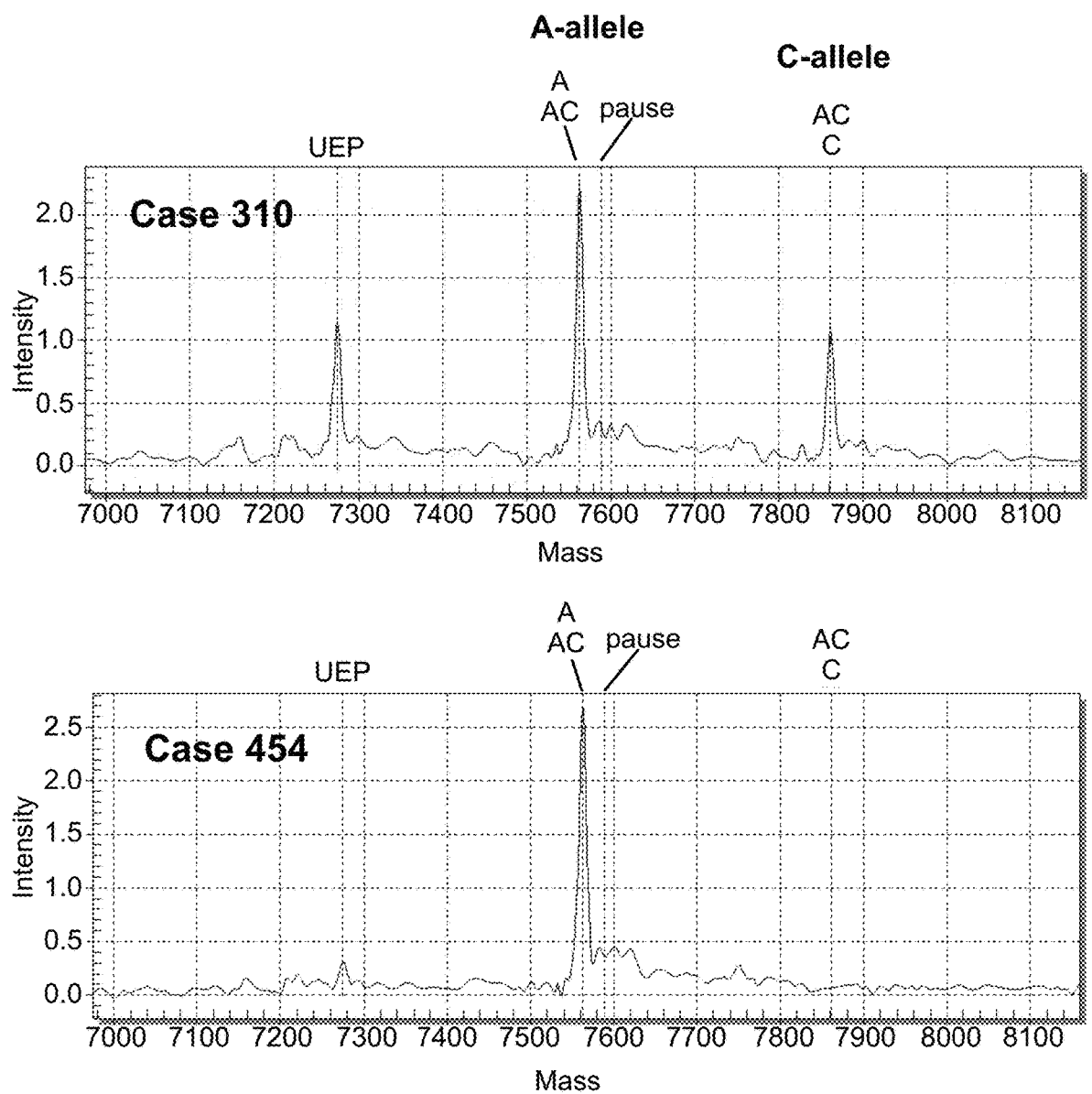
FIG. 11. Mass spectrometric tracings of maternal plasma U-maspin −156 SNP genotype in cases 310 and 454. The corresponding maternal blood cell and placental tissue genotypes for the two cases are shown in Table 1. In both mass spectra, the x-axis depicts the molecular weight of the detected extension products (shown as sharp peaks), while the y-axis depicts the intensity in arbitrary units. The expected positions of the A- and C-alleles are as marked.

The −156 SNP is an A/C polymorphism. The fetal and maternal maspin genotypes, shown in Table 1, were determined from 8 third-trimester pregnancies using genomic DNA collected from placental tissues and the corresponding maternal blood cells. A MassEXTEND assay was designed to interrogate the −156 SNP among U-maspin promoter sequences. The A-allele of the −156 SNP would be extended by one base while the C-allele would be extended by two bases (FIG. 4) which are resolved as peaks of different masses on MS (FIG. 11). Maternal plasma samples from the eight pregnancies were bisulfite converted and the U-maspin −156 SNP genotype was assessed. The maternal plasma U-maspin genotypes were completely concordant with that of the placental tissues (Table 1). These data confirm that U-maspin in maternal plasma is derived from the placenta.

To demonstrate the specificity of the MassEXTEND assay towards U-maspin, bisulfite converted maternal blood cells, which comprised predominantly of M-maspin, were also analyzed. No false-positive amplification from any of the maternal blood cell samples was noted (data not shown). Mass spectrometric tracings for maternal plasma U-maspin genotyping for two representative cases are shown in FIG. 11.

TABLE 1

Genotype analysis of U-maspin in maternal plasma

| | Maspin promoter −156 SNP genotype | | |
|---|---|---|---|
| | Genomic DNA | | Bisulfite converted DNA |
| Case | Maternal | Fetal | Maternal plasma U-maspin |
| 258 | A | A | A |
| 272 | AC | AC | AC |
| 300 | A | AC | AC |
| 310 | A | AC | AC |
| 331 | AC | AC | AC |
| 340 | AC | A | A |
| 427 | AC | A | A |
| 454 | AC | A | A |

Non-Invasive Prenatal Diagnosis of Trisomy 18

The use of the U-maspin system for the non-invasive prenatal diagnosis of trisomy 18 is illustrated in FIG. 5. This strategy is possible because the maspin gene is located on chromosome 18. One embodiment of this strategy is the use of primer sequences which amplify unmethylated maspin sequences from maternal plasma. As demonstrated above these sequences are predominantly derived from the fetus. The primer sequences are designed such that they encompass one or more polymorphisms. By means of illustration, one possible type of polymorphism is the single nucleotide polymorphism (SNP). As a further illustration of this strategy, if the fetus is heterozygous at the detected polymorphism, then the allelic ratio of the detected alleles can be measured, possibly by primer extension and mass spectrometry, or by other methods known to those skilled in the art. In one scenario, if the fetus has the normal situation of two chromosome 18, then the allelic ratio will be 1 to 1. If the fetus has the abnormal situation of three chromosome 18 (i.e., trisomy 18), then the allelic ratio will deviate from 1 to 1. As another illustration of this, the allelic ratio may become 2 to 1 or 1 to 2.

Figure 12:
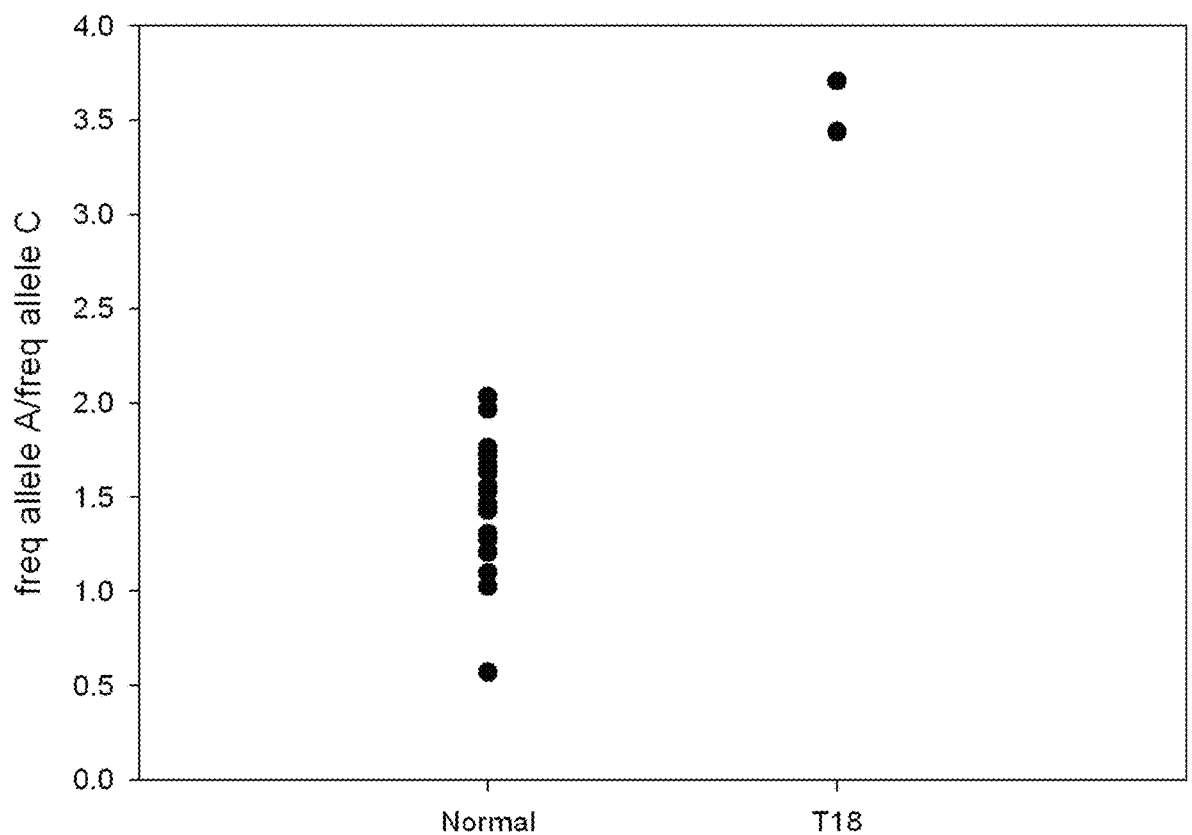
FIG. 12. Scatter plot of the ratios of the −156 SNP among placental U-maspin sequences in normal pregnancies and pregnancies involving a trisomy 18 fetus (T18). The ratios are determined by comparing the area of the peaks for each respective allele on the mass spectra.

Gene dosage of U-maspin for 23 normal pregnancies and 2 pregnancies involving a trisomy 18 fetus was determined using the MassEXTEND assay which targets the −156 SNP among unmethylated maspin sequences. The fetuses of all these pregnancies are confirmed to be heterozygous for the SNP based on genotype analysis on genomic DNA extracted from placental tissues. To assess the gene dosage of U-maspin, bisulfite-converted placental tissue DNA was assessed by the MassEXTEND assay. The SNP allelic ratio was determined by comparing the area of the peaks for the respective alleles on the mass spectra. The ratio between the two alleles among the trisomy 18 pregnancies deviated from that of the normal pregnancies (FIG. 12).

Figure 13:
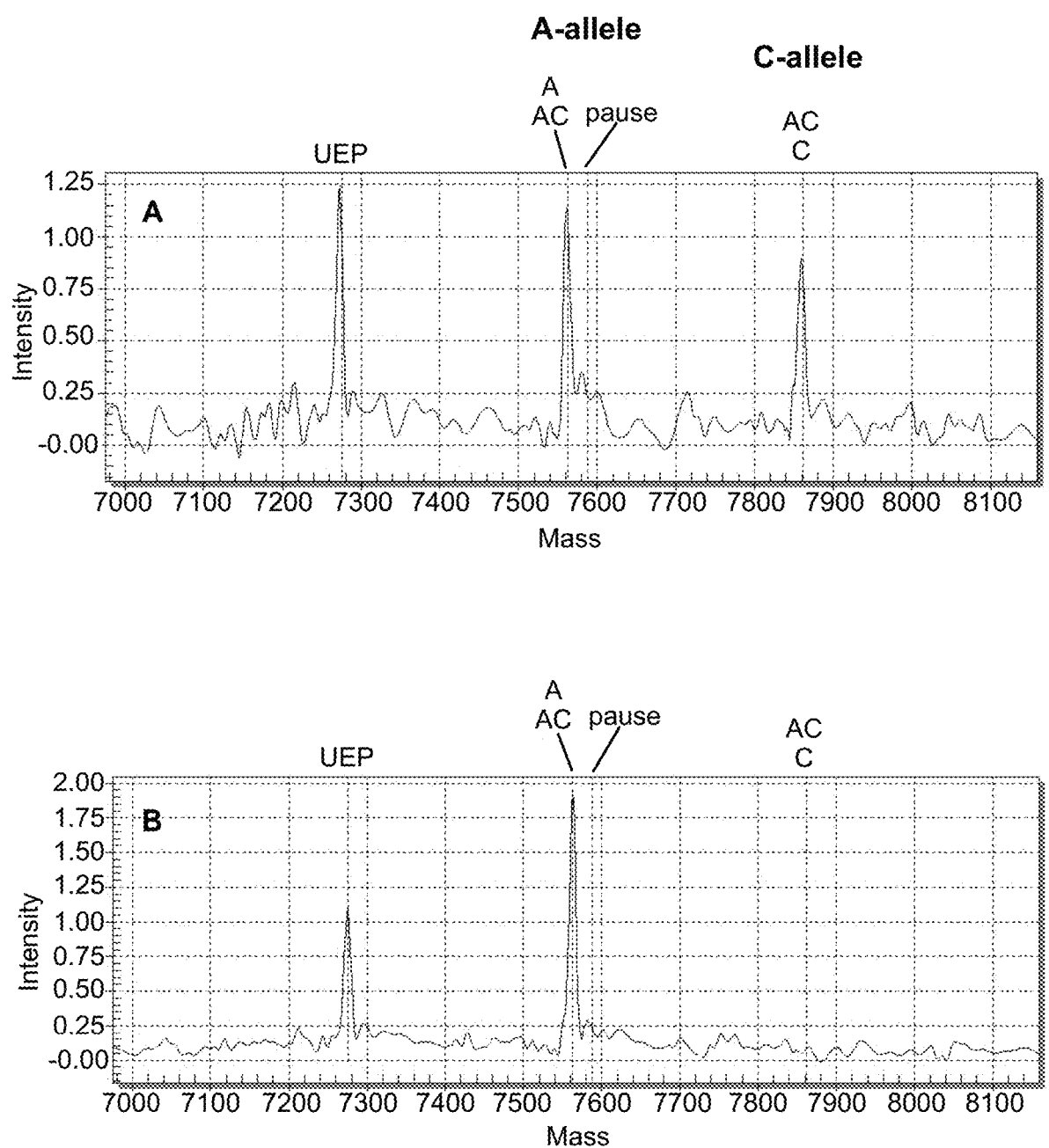
FIG. 13. Mass spectrometric tracing illustrating the U-maspin −156 SNP allelic frequency in two sample mixtures containing 95% DNA from maternal blood cells and 5% DNA from placental tissues obtained from pregnancies involving a karyotypically normal fetus. The x-axis depicts the molecular weight of the detected extension products (shown as sharp peaks), while the y-axis depicts the intensity in arbitrary units. The expected positions of the A- and C-alleles are as marked.

To demonstrate the reliability of the assay and the strategy for allelic ratio determination in samples containing a minority fraction of fetal DNA with a high background of maternal DNA, the assay was applied to two sample mixtures comprised of 95% DNA from a maternal blood cell sample and 5% DNA from the corresponding placental tissue. Both pregnancies were confirmed to be karyotypically normal. The results are shown in FIG. 13. Case A represents a pregnancy involving a mother homozygous for the A-allele and a heterozygous fetus at the maspin −156 SNP, and vice versa for case B. The lack of detection of the maternal C-allele for case B confirms the fetal-specifcity of the assay. The A:C allelic ratio for case A was 1.235 which is within the range of values obtained for karyotypically normal pregnancies (FIG. 12). These data confirm the applicability of the assay for allelic ratio determination in biological samples containing fetal DNA within a high background of maternal DNA, one example being fetal DNA in maternal plasma.

All patents, patent applications, and other publications cited in this application, including published amino acid or polynucleotide sequences, are incorporated by reference in the entirety for all purposes.

What is claimed is:

1. A method of analyzing the maspin gene in the blood of a pregnant woman, comprising the steps of
   (a) isolating DNA from a blood sample taken from a pregnant woman;
   (b) treating the DNA from step (a) with a reagent that differentially modifies methylated and non-methylated DNA, thereby distinguishing methylated and unmethylated version of the maspin gene; and
   (c) performing an amplification reaction to amplify at least one portion of the unmethylated version of the maspin gene.

2. The method of claim 1, further comprising, prior to step (a), obtaining the blood sample from the woman.

3. The method of claim 1, wherein the DNA is acellular DNA in the blood sample.

4. The method of claim 1, wherein the blood sample is whole blood.

5. The method of claim 1, wherein the blood sample is plasma or serum.

6. The method of claim 1, wherein the blood sample is obtained from the woman after 10 weeks of gestation.

7. The method of claim 1, wherein the reagent comprises bisulfate.

8. The method of claim 1, wherein the reagent comprises one or more enzymes that preferentially cleave methylated DNA.

9. The method of claim 1, wherein the reagent comprises one or more enzymes that preferentially cleave unmethylated DNA.

10. The method of claim 1, wherein the amplification reaction is a polymerase chain reaction (PCR).

11. The method of claim 10, wherein the PCR is a methylation-specific PCR.

12. The method of claim 10, wherein the PCR is real-time PCR.

13. The method of claim 1, wherein the amplification reaction is a nucleic acid sequence based amplification, a strand displacement reaction, or a branched DNA amplification reaction.

14. The method of claim 1, wherein step (c) further comprises sequencing the amplified at least one portion of the unmethylated version of the maspin gene.

15. The method of claim 14, wherein step (c) comprises mass spectrometry, primer extension, polynucleotide hybridization, or electrophoresis.

16. The method of claim 1, wherein the at least one portion of the maspin gene is the promoter region of the maspin gene.

* * * * *

SEQUENCE LISTING

```
<160> NUMBER OF SEQ ID NOS: 10

<210> SEQ ID NO 1
<211> LENGTH: 300
<212> TYPE: DNA
<213> ORGANISM: Homo sapiens
<220> FEATURE:
<223> OTHER INFORMATION: human maspin (serine (or cysteine) proteinase
      inhibitor, serpin peptidase inhibitor, clade B
      (ovalbumin), member 5, serpin B5) promoter
      sequence fully methylated at all CpG sites
<220> FEATURE:
<221> NAME/KEY: modified_base
<222> LOCATION: (91)
<223> OTHER INFORMATION: m5c
<220> FEATURE:
<221> NAME/KEY: modified_base
<222> LOCATION: (144)
<223> OTHER INFORMATION: m5c
<220> FEATURE:
<221> NAME/KEY: modified_base
<222> LOCATION: (160)
<223> OTHER INFORMATION: m5c
<220> FEATURE:
<221> NAME/KEY: modified_base
<222> LOCATION: (168)
<223> OTHER INFORMATION: m5c
<220> FEATURE:
<221> NAME/KEY: modified_base
<222> LOCATION: (175)
<223> OTHER INFORMATION: m5c
<220> FEATURE:
<221> NAME/KEY: modified_base
<222> LOCATION: (187)
<223> OTHER INFORMATION: m5c
<220> FEATURE:
<221> NAME/KEY: modified_base
<222> LOCATION: (191)
<223> OTHER INFORMATION: m5c
<220> FEATURE:
<221> NAME/KEY: modified_base
<222> LOCATION: (203)
<223> OTHER INFORMATION: m5c
<220> FEATURE:
<221> NAME/KEY: modified_base
<222> LOCATION: (235)
<223> OTHER INFORMATION: m5c

<400> SEQUENCE: 1
tgggtagtta ttttttttgg tatttagtag aatgagttgt tgtagtttat ataaaaagaa      60
tggagattag agtatttttt gtgttattaa cgtgtttgag aaatttgtag tgttattatt     120
attatatatt attttattt tatcgaatat tttattttc ggttttgcgt gggtcgagag      180
gattgtcgta cgtatgtttg tacgtatgta tgtaatttat agttttttt tgttcgaata     240 tgttggaggt ttttggaag ttgtgtagat aatagtaatt ttagtttgaa ttatttttt     300

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence:bisulfite
      sequencing primer F
```

<400> SEQUENCE: 2
gaatggagat tagagtattt tttgtgttat                                    30

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:bisulfite
      sequencing primer R

<400> SEQUENCE: 3
atatgttgga ggtttttggg aagt                                          24

<210> SEQ ID NO 4
<211> LENGTH: 29
<212> TYPE: DNA
<213> ORGANISM: Artificial Sequence
<220> FEATURE:
<223> OTHER INFORMATION: Description of Artificial
      Sequence:methylation-specific PCR (MSP) assay
      specific for methylated maspin (MMSP) primer MF

<400> SEQUENCE: 4
ttatcgaata ttttattttt cggtttcgc                                     29

<210> SEQ ID NO 5
<211> LENGTH: 38
<212> TYPE: DNA
<213> ORGANISM: Artificial Sequence
<220> FEATURE:
<223> OTHER INFORMATION: Description of Artificial
      Sequence:methylation-specific PCR (MSP) assay
      specific for methylated maspin (MMSP) primer MR

<400> SEQUENCE: 5
gcgtacaaac atgcatacat acattaaata tcaaaaaa                           38

<210> SEQ ID NO 6
<211> LENGTH: 36
<212> TYPE: DNA
<213> ORGANISM: Artificial Sequence
<220> FEATURE:
<223> OTHER INFORMATION: Description of Artificial
      Sequence:methylation-specific PCR (MSP) assay
      specific for unmethylated maspin (UMSP) primer UF

<400> SEQUENCE: 6
ttttatttta ttgaatattt tattttttgg tttcgt                             36

<210> SEQ ID NO 7
<211> LENGTH: 40
<212> TYPE: DNA
<213> ORGANISM: Artificial Sequence
<220> FEATURE:
<223> OTHER INFORMATION: Description of Artificial
      Sequence:methylation-specific PCR (MSP) assay
      specific for unmethylated maspin (UMSP) primer UR

<400> SEQUENCE: 7
acgtacaaac atacatacat acattaaata tcaaaaaaaa                         40

<210> SEQ ID NO 8
<211> LENGTH: 17
<212> TYPE: DNA
<213> ORGANISM: Artificial Sequence

```
<220> FEATURE:
<223> OTHER INFORMATION: Description of Artificial Sequence:real-time
      quantitative methylation-specific PCR (MSP) assay
      specific for methylated maspin (MMSP) TaqMan Minor
      Groove Binding (MGB) probe MP

<400> SEQUENCE: 8
tgggtygaga ggattgt                                                   17

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence:real-time
      quantitative methylation-specific PCR (MSP) assay
      specific for unmethylated maspin (UMSP) TaqMan
      Minor Groove Binding (MGB) probe UP

<400> SEQUENCE: 9
tgggttgaga ggattgt                                                   17

<210> SEQ ID NO 10
<211> LENGTH: 46
<212> TYPE: DNA
<213> ORGANISM: Artificial Sequence
<220> FEATURE:
<223> OTHER INFORMATION: Description of Artificial Sequence:T/A single
      nucleotide polymorphism (SNP) from A/C SNP
      bisulfite converted and interrogated in reverse

<400> SEQUENCE: 10
ggtcgagagg wttgtcgtac gtatgtttgt acgtatgtat gtaatt                   46
```